(12) United States Patent
Dissing et al.

(10) Patent No.: US 8,911,342 B2
(45) Date of Patent: Dec. 16, 2014

(54) APPARATUS AND METHOD FOR PULSED ELECTRICAL FIELD TREATMENT

(75) Inventors: Steen Dissing, Charlottenlund (DK); Mogens Unden, Hornbæk (DK)

(73) Assignee: Re5 ApS, Frederiksberg C (DK)

( * ) Notice: Subject to any disclaimer, the term of this patent is extended or adjusted under 35 U.S.C. 154(b) by 309 days.

(21) Appl. No.: 13/380,381

(22) PCT Filed: Jun. 22, 2010

(86) PCT No.: PCT/DK2010/050154
§ 371 (c)(1),
(2), (4) Date: Dec. 22, 2011

(87) PCT Pub. No.: WO2010/149164
PCT Pub. Date: Dec. 29, 2010

(65) Prior Publication Data
US 2012/0101327 A1 Apr. 26, 2012

Related U.S. Application Data

(60) Provisional application No. 61/219,228, filed on Jun. 22, 2009.

(30) Foreign Application Priority Data

Jun. 23, 2009 (DK) .................................. 2009 70035

(51) Int. Cl.
*A61N 1/00* (2006.01)
*A61K 41/00* (2006.01)
*A61N 2/02* (2006.01)
*A61N 2/00* (2006.01)

(52) U.S. Cl.
CPC . *A61K 41/00* (2013.01); *A61N 2/02* (2013.01); *A61N 2/006* (2013.01); *A61N 2/002* (2013.01)
USPC .............................................. 600/14; 607/45

(58) Field of Classification Search
USPC ........................................... 600/9–15; 607/45
See application file for complete search history.

(56) References Cited

U.S. PATENT DOCUMENTS 6,132,361 A 10/2000 Epstein et al.
6,425,852 B1 7/2002 Epstein et al.
(Continued)

FOREIGN PATENT DOCUMENTS

EP 1 216 076 8/2006
EP 1 894 600 3/2008
(Continued)

OTHER PUBLICATIONS

Martiny, "Pulsed Electromagnetic Fields in Treatment Resistant Depression. A Pilot Study", Journal of Affective Disorders, vol. 78, No. Supplement 1, Mar. 2004, pp. S124-S125.
(Continued)

*Primary Examiner* — Charles A Marmor, II
*Assistant Examiner* — Carrie R Dorna
(74) *Attorney, Agent, or Firm* — Pearl Cohen Zedek Lazter Baratz LLP

(57) ABSTRACT

The present invention concerns an apparatus and a method for stimulating brain tissue with pulsed electromagnetic fields weaker than the limit for elicitation of the action potentials of the cells of the tissue to be stimulated, the apparatus comprising: at least one electrically conducting coil positioned at a bitemporal position such that hippocampus is stimulated by at least one magnetic field upon supplying a pulse to said coil as well as a coil positioned at a occipital and parietal position; and a pulse generation means operationally connected to said at least one coil for supplying a series of current pulses for conduction, allowing generation of pulsed electromagnetic fields sufficiently strong to cause protein activation, and weaker than the limit for elicitation of the action potentials of the cells of the tissue to be stimulated.

11 Claims, 9 Drawing Sheets

Placement of the seven coils

Frontal view   Posterior view

(56) References Cited

U.S. PATENT DOCUMENTS

| | | |
|---|---|---|
| 6,561,968 B1 | 5/2003 | Dissing et al. |
| 2003/0050527 A1 | 3/2003 | Fox et al. |
| 2004/0122281 A1 | 6/2004 | Fischell et al. |
| 2005/0154426 A1* | 7/2005 | Boveja et al. .................. 607/45 |
| 2006/0205993 A1 | 9/2006 | Fischell et al. |
| 2007/0203390 A1 | 8/2007 | Rohan et al. |
| 2009/0156884 A1 | 6/2009 | Schneider et al. |

FOREIGN PATENT DOCUMENTS

| | | |
|---|---|---|
| EP | 1 977 787 | 1/2010 |
| WO | WO 01/15774 | 3/2001 |
| WO | WO 02/09811 | 2/2002 |

OTHER PUBLICATIONS

Bretlau, et al., "Repetitive Transcranial Magnetic Stimulation (rTMS) in Combination with Escitalopram in Patients with Treatment-resistant Major Depression: A Double-blind, Randomised, Sham-controlled Trial", Database Accession No. NLM18311683 and Pharmacopsychiatry Mar. 2008 LNKD-PUBMED: 18311683, vol. 41, No. 2, Mar. 2008, pp. 41-47.

Thamsborg et al., "Treatment of Knee Osteoarthritis with Pulsed Electromagnetic Fields: A Randomized, Double-blind, Placebo-controlled Study", Osteoarthritis and Cartilage, 2005, 13(7), pp. 575-581.

Rahbek et al., "Interactions of Low-Frequency, Pulsed Electromagnetic Fields with Living Tissue: Biochemical Responses and Clinical Results", Oral Biosciences, vol. 2, No. 1, 2005, pp. 1-12.

Kozisek et al., "Brain-derived Neurotrophic Factor and its Receptor Tropomyosin-related Kinase B in the Mechanism of Action of Antidepressant Therapies", Pharmacology & Therapeutics, 2008, 117(1), pp. 30-51.

Evans et al., "Dysregulation of the Fibroblast Growth Factor System in Major Depression", Proc Natl Acad Sci USA, Oct. 26, 2004, vol. 101, No. 43, pp. 15506-15511.

CRS Report for Congress, The National Institutes of Health, "Stem Cell Research: Federal Research Funding and Oversight", 2001, pp. CRS-1-CRS-27.

Martiny, "Pulsed Electromagnetic Fields in Treatment Resistant Depression". A Pilot Study, Journal of Affective Disorders, vol. 78, Supplement 1, Mar. 2004, pp. S124-S125.

Bretlau, et al., "Repetitive Transcranial Magnetic Stimulation (rTMS) in Combination with Escitalopram in Patients with Treatment-Resistant Major Depression: A Double-Blind, Randomised, Sham-Controlled Trial", Pharmacopsychiatry 2008, vol. 41, No. 2, Mar. 2008, pp. 41-47.

Rubin, et al., "Optimization of Electric Field Parameters for the Control of Bone Remodeling: Exploitation of an Indigenous Mechanism for the Prevention of Osteopenia", Journal of Bone and Mineral Research, vol. 8, Supplement 2, 1993, pp. S573-S581.

\* cited by examiner

US 8,911,342 B2

APPARATUS AND METHOD FOR PULSED ELECTRICAL FIELD TREATMENT

CROSS-REFERENCE TO RELATED APPLICATIONS

This application is a National Phase Application of PCT International Application No. PCT/DK2010/050154, entitled "APPARATUS AND METHOD FOR PULSED ELECTRICAL FIELD TREATMENT", International Filing Date Jun. 22, 2010. published on Dec. 29, 2010 as International Publication No. WO 2010/149164, which in turn claims priority from U.S. Provisional Patent Application No. 61/219,228, filed Jun. 22, 2009 and Danish Patent Application No. PA 2009 70035, filed Jun. 23, 2009, all of which are incorporated herein by reference in their entirety.

FIELD OF THE INVENTION

The present invention provides a method and an apparatus for treatment tissue with pulsed electrical fields. In particular, it provides a method and an apparatus for stimulating cellular activities in brain tissue causing improved neural function for patient suffering from mental disorders.

BACKGROUND OF THE INVENTION

Pulsed electromagnetic fields (PEMF) have been used widely to activate cellular signalling and have been implicated in a number of disease treatments including, delayed non-heating fractures, pseudoarthrosis, osteoarthritis, bone fractures and related problems and have also been suggested for the treatment of nerve growth and wound healing.

U.S. Pat. No. 6,561,968 describes a method and apparatus that utilises the electromotoric force imposed on tissue by a unique combination of coils arrangements.

The application US 2003/50527 describes devices and methods for transcranial magnetic stimulation, "TMS". TMS is described as a means for repetitively stimulating the human brain through an intact scalp and skull, i.e. non-invasively. TMS is delivered by passing a brief (200 microsecond), strong (10 kV, 6000 A) electrical current through a coil of wire (a TMS stimulator) placed adjacent to the head. The passage of electrical current induces a strong (2 Tesla) magnetic field which induces electrical currents in nearby tissues. In particular, this application concerns rapid rate transcranial magnetic stimulation (rTMS) using a repetition rate of 10 Hz. The stimulator output is set to 110% of relaxed motor threshold. Stimulation is delivered in ten trains of 5 seconds each, with trains beginning 30 seconds apart. Treatment is administered once daily for five consecutive weekdays.

U.S. Pat. No. 6,425,852 describes use of rapid rate transcranial magnetic stimulation with a frequency of 1 Hz or 5 Hz for the treatment of depression, apparently suggesting the use of strong magnetic fields in the Tesla range.

SUMMARY OF THE INVENTION

It is the object of the present invention to provide a method and apparatus that stimulates neural tissues and substantially overcomes one or more of the problems due to the limited biological activity under certain conditions.

It has surprisingly been discovered that a high number of weak pulsating electromagnetic fields may have a positive effect on depressions, in particular when used in combination with anti-depressive medication.

Without being bound by any theory, the inventors of the present invention speculates that the fluctuating electromagnetic fields will induce an electric field in the tissue, and that capillary endothelial cells as well as neural tissue show enhanced cellular activity related to c-Src protein kinase activity as well as the mitogen activated protein kinase activity (MAPK) when under influence of such electric field. In combination with inhibitors of reuptake of transmitters it leads to enhanced mRNA transcription leading to synthesis of growth factors and cytokines. These are then released in a paracrine fashion. The result is enhanced cellular activity of neural tissue as well as an enhanced angiogenesis and blood flow. The result is improved condition for patients suffering from depressions including bipolar disorders. This has been shown in a double blind placebo controlled study.

Some of the principles used for developing the present apparatus have been disclosed in U.S. Pat. No. 6,561,968 and EP 1216076, hereby incorporated by reference in their entirety. These patents disclose an apparatus which includes a pulse generator and seven coils, in which pulsed currents cause fluctuating magnetic fields in a predetermined region. A similar apparatus may be adapted to stimulate brain tissue.

Thus, one aspect of the invention relates to an apparatus for stimulating brain tissue with pulsed electromagnetic fields weaker than the limit for elicitation of the action potentials of the cells of the tissue to be stimulated, said apparatus comprising:

1. at least one electrically conducting coil at a bitemporal position such that hippocampus is stimulated by at least one magnetic field upon supplying a pulse to said coil; and
2. a pulse generation means operationally connected to said at least one coil for supplying a series of current pulses for conduction, allowing generation of pulsed magnetic fields sufficiently strong to cause protein activation, and weaker than the limit for elicitation of the action potentials of the cells of the tissue to be stimulated.

This aspect represents the basic idea of the invention.

In a preferred embodiment, the first aspect provides an apparatus for stimulating brain tissue with pulsed induced electrical fields induced by time-varying magnetic fields generated by the apparatus, said apparatus comprising:

at least five, such as preferably six, electrically conducting coils arranged in a device to be worn on a subject's head so that the axes of the coils point into the head; and a pulse generation means operationally connected to said one or more coils for supplying a series of bipolar square voltage pulses to each coil resulting in a generation of a time-varying magnetic field from each coil;

characterized in that the pulses and the coils being selected so that the time-varying magnetic field induces an electrical field sufficiently strong to cause protein activation, and weaker than a limit for elicitation of the action potentials of cells of the brain tissue to be stimulated, in that the electric field strength in a plane perpendicular to each coil, a maximum field strength falls in the interval $0.5 \times 10^{-6}$–0.5 V/m at a distance of 10 cm from each coil;

the pulse generation means being configured to apply treatment in doses with a bipolar square pulses supplied at a frequency of at least 20 Hz over a period of 5-120 minutes;

at least four of the coils being arranged in the device such that hippocampus is stimulated by the induced electrical field upon supplying pulses to said four coils; and at least one, such as preferably two, of the coils being arranged in the device such that cortex is stimulated by the induced electrical field upon supplying pulses to said two coils, said coil having frontal placement.

In a preferred embodiment, the apparatus further comprising at least one coil having occipital placement. This provides the advantage that the induced electrical field induced by supplying pulses to said at least one coil will stimulate serotonergic neurons.

In this respect, the coils being arranged in the device such that hippocampus is stimulated upon use preferably means that the coils are arranged so that axes of the coils intersect the hippocampus of the subject, or arranged to have temporal and/or parietal placements, preferably so that axes of the coils intersect the temporal and/or parietal lobes of the subject. In an alternative wording, the coils are arranged in two sets of two coils being positioned above the ears of the subject, or in case of more than four coils, regularly distributed above the ears of the subject.

Also in this respect, the coil(s) being arranged in the device such that cortex is stimulated upon use preferably means that the coil(s) are arranged so that axes of the coil(s) intersect(s) the cortex of the subject, or arranged to have frontal placement(s), preferably so that axes of the coil(s) intersect(s) the frontal lobe of the subject. In an alternative wording, the coil is arranged at the upper part of the subject's head, or in case of two coils, arranged on each side of an upper part of the subject's head, or, in case of more than two coils, regularly distributed on the upper part of the subject's head.

Also in this respect, the at least one coil being arranged in the device such that serotonergic neurons are stimulated upon use preferably means that the at least one coils has occipital placement, preferably so that axes of the coils intersects the occipital lobe of the subject. In an alternative wording, the at least one coil is arranged at the lower back part of the subject's head, or, in case of more than one coil, regularly distributed on the lower back part of the subject's head.

Another aspect of the present invention relates to a kit comprising an apparatus according to the invention, accompanied by instructions to use said apparatus for the treatment of depression. In a preferred embodiment, the instructions may further comprises instructions for combining the treatment with a pharmaceutical for the treatment of depression.

Yet another aspect of the present invention is to provide the use of a pulsed electromagnetic field applied trans-cranially at the bitemporal area of a subject for the treatment or prophylaxis of a condition selected from the group consisting of depression, major depressive disorder, bipolar disorder/manio depression, epilepsy, Parkinson's disease and Alzheimer's disease and/or for alleviating one or more symptoms associated with said condition.

Still another aspect of the present invention is to provide the use of an antidepressant substance or compound for the manufacture of a medicament for preventing, treating or relieving a disorder selected from the group consisting of Depression, Major Depressive Disorder, Bipolar Disorder, Epilepsy, Parkinson's Disease and Alzheimer's Disease in a subject and/or for alleviating one or more symptoms associated with said disease, said subject receiving treatment by application of a pulsed electromagnetic field trans-cranially to the hippocampus and optionally to the cerebellum and/or the frontal lobes.

Yet an aspect of the invention concerns an antidepressant substance or compound for use in prophylaxis, treatment or relief of a disorder selected from the group consisting of Depression, Major Depressive Disorder, Bipolar Disorder, Epilepsy, Parkinson's Disease and Alzheimer's Disease in a subject and/or for alleviating one or more symptoms associated with said disease, concomitant or in connection with treatment of said subject by application of a pulsed electromagnetic field trans-cranially to the hippocampus and optionally to the cerebellum and/or the frontal lobes of said subject.

An additional aspect of the invention concerns a method, such as a non-invasive method, for the treatment or prophylaxis of a condition selected from the group consisting of Depression, Major Depressive Disorder Bipolar Disorder, Epilepsy, Parkinson's disease and Alzheimer's disease and/or for alleviating one or more symptoms associated therewith in a subject, said method comprising a step of applying a pulsed electromagnetic field trans-cranially at the bi-temporal area to the hippocampus and optionally to the parietal and/or occipital area of said subject.

BRIEF DESCRIPTION OF THE FIGURES

FIG. 1A illustrates the current output signal resulting from bipolar square voltage pulse pairs from the pulse generator.

Figure 1:
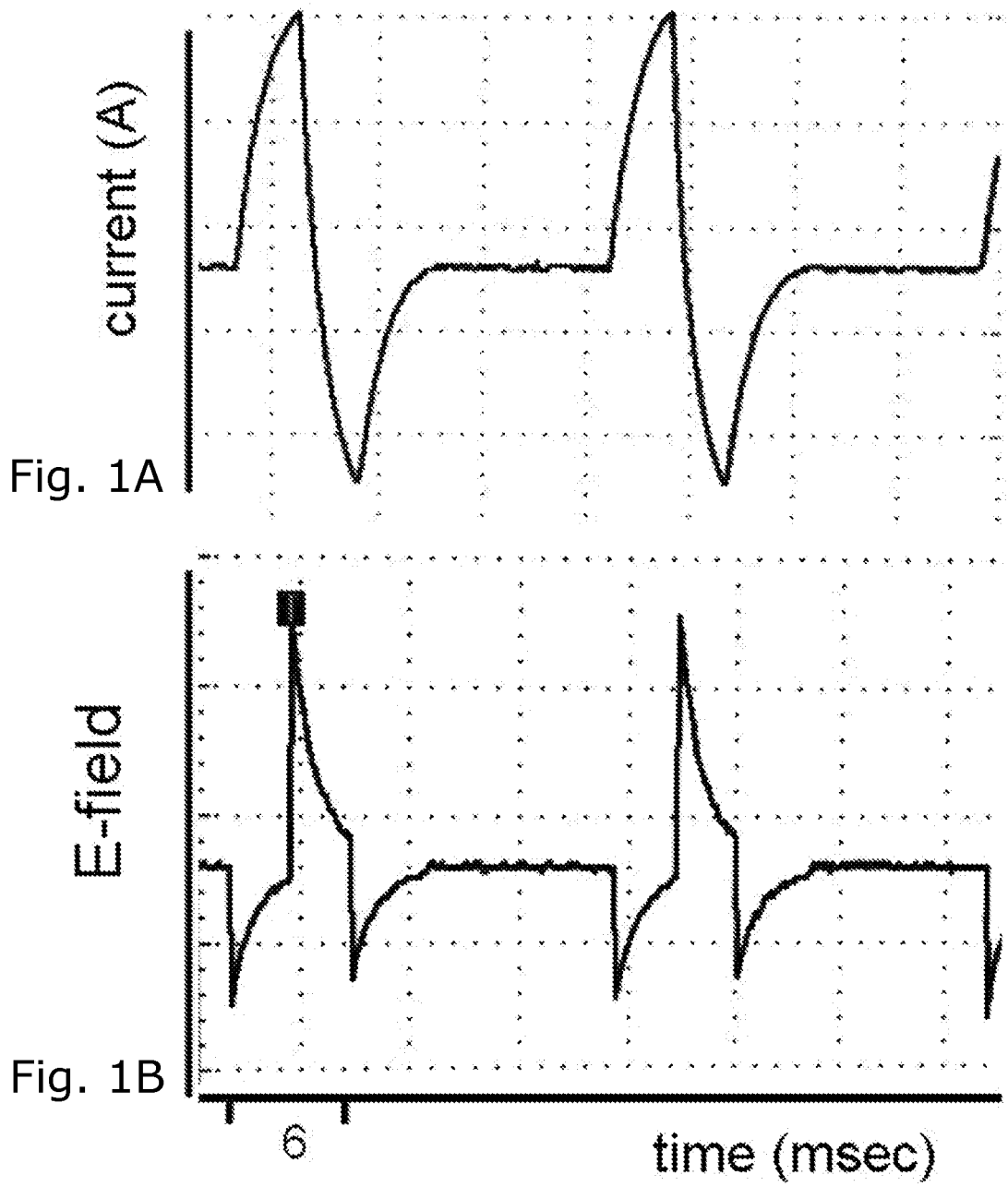
FIGS. 1A and B show a coil and induced E-field characteristics.
FIG. 1B is the resulting shape of the induced E-field pulses as measured in a sense coil. The E-field is proportional to the change in current and thereby magnetic field (B). Thus, E-field=dB/dt.

The present invention will now be described in more detail in the following.

DETAILED DESCRIPTION OF THE INVENTION

According to an aspect, the invention concerns an apparatus for stimulating brain tissue with pulsed electromagnetic fields weaker than the limit for elicitation of the action potentials of the cells of the tissue to be stimulated, said apparatus comprising:
- at least one electrically conducting coil positioned bitemporally such that hippocampus is stimulated by at least one magnetic field upon supplying a pulse to said coil; and
- a pulse generation means operationally connected to said at least one coil for supplying a series of current pulses for conduction, allowing generation of pulsed electromagnetic fields sufficiently strong to cause protein activation, and weaker than the limit for elicitation of the action potentials of the cells of the tissue to be stimulated.

The brain tissue is subjected to transcranial stimulation. Preferably, at least one electrically conducting coil is selectively stimulating the hippocampus. Using weak magnetic fields avoids elicitation of the action potentials of the cells. It further allows manufacture of a small, portable and inexpensive equipment. Using weaker fields means that metal objects may be carried closer to the equipment, and means lesser energy requirements of the apparatus.

Preferably, the induced electromagnetic fields are far weaker than necessary for elicitation of the action potentials of the cells, such as 2 times weaker, more preferred 5 times weaker, preferably 10 times weaker, more preferred 50 times weaker, preferably 100 times weaker, more preferred 500 times weaker, preferably 1000 times weaker, more preferred 5000 times weaker, preferably 10,000 times weaker, more preferred 50,000 times weaker, preferably 100,000 times weaker, more preferred 500,000 times weaker, preferably 1,000,000 times weaker.

Strong fields imply a further number of disadvantages, as apparent e.g. from U.S. Pat. No. 6,425,852, including pain for patients being treated, speech arrest, motor tics, periodic limb flexion, paresthesias, as well as mild headache in a number of patients. The heating of tissue is another drawback associated with strong fields.

Further, strong fields may in some cases not be administered to patients with a history of recent myocardial infarction, cardiac pacemaker, intracranial objects or increased intracranial pressure.

An embodiment of the invention concerns an apparatus according to the invention for the treatment of depression.

Such an apparatus has proven especially useful for use in combination with medication, such as SSRI, for the treatment of depression, in particular in patients which do not respond to treatment with the medication alone.

Pulsed electromagnetic fields (PEMF) may be used to activate cellular signalling. Proteins become activated leading to angiogenic processes, increased blood flow as well as a number of other parameters such as enhanced growth of bone tissue.

A temporarily varying magnetic flux through an area induces an electric field, E, along the perimeter of the area according to the basic laws of electromagnetism. If the varying magnetic field, B(t), is applied to a material containing free (or mobile) charge carriers, these will be accelerated in the induced electric fields, which leads to electric currents in the tissue. Proteins with positive and negative charges as well as on electrically charged second messengers that participate in cell signalling will also be accelerated. The induced electric field, or the tissue currents generated thereby, depends upon the rate of change, dB/dt, of the magnetic field, the electric field or current increasing with increasing rate of change. The inventors have surprisingly discovered that this may be used clinically, as the cytoplasmic tyrosin kinase, Src, becomes activated by the pulsed electrical fields and that in turn directs signalling dependent on cells type and signalling network.

In the U.S. Pat. No. 6,561,968 the inventors applied the above mentioned pulsed induced electrical fields that are small ($1\times10^{-3}$–10 V/m). The pulse pattern are shown in FIG. 1 with the current in coil as well as the induced E-field as measured by use of a sense coil, proportional to the change in the magnetic field strength (dB/dt). The sharp rise in the induced E-field following the voltage change from +50V to −50V is one of the essential features of the pulse pattern. A relative placement of coils, e.g. as described in U.S. Pat. No. 6,561,968 ensures the synchrony in pulse activation and pulse intensity in nervous tissue.

In a preferred embodiment, the pulse generating mean is a voltage pulse generator for generating bipolar square voltage pulses. The amplitude depends on the dimensions of the coils, but in a preferred embodiment, the bipolar square pulses start with +50 V for e.g. 3 ms followed by −50 V for 3 ms. As a consequence the current pulses as depicted in FIG. 1A arises in the coils, which again are capable of inducing the electrical fields depicted in FIG. 1B in tissue.

Figure 2:
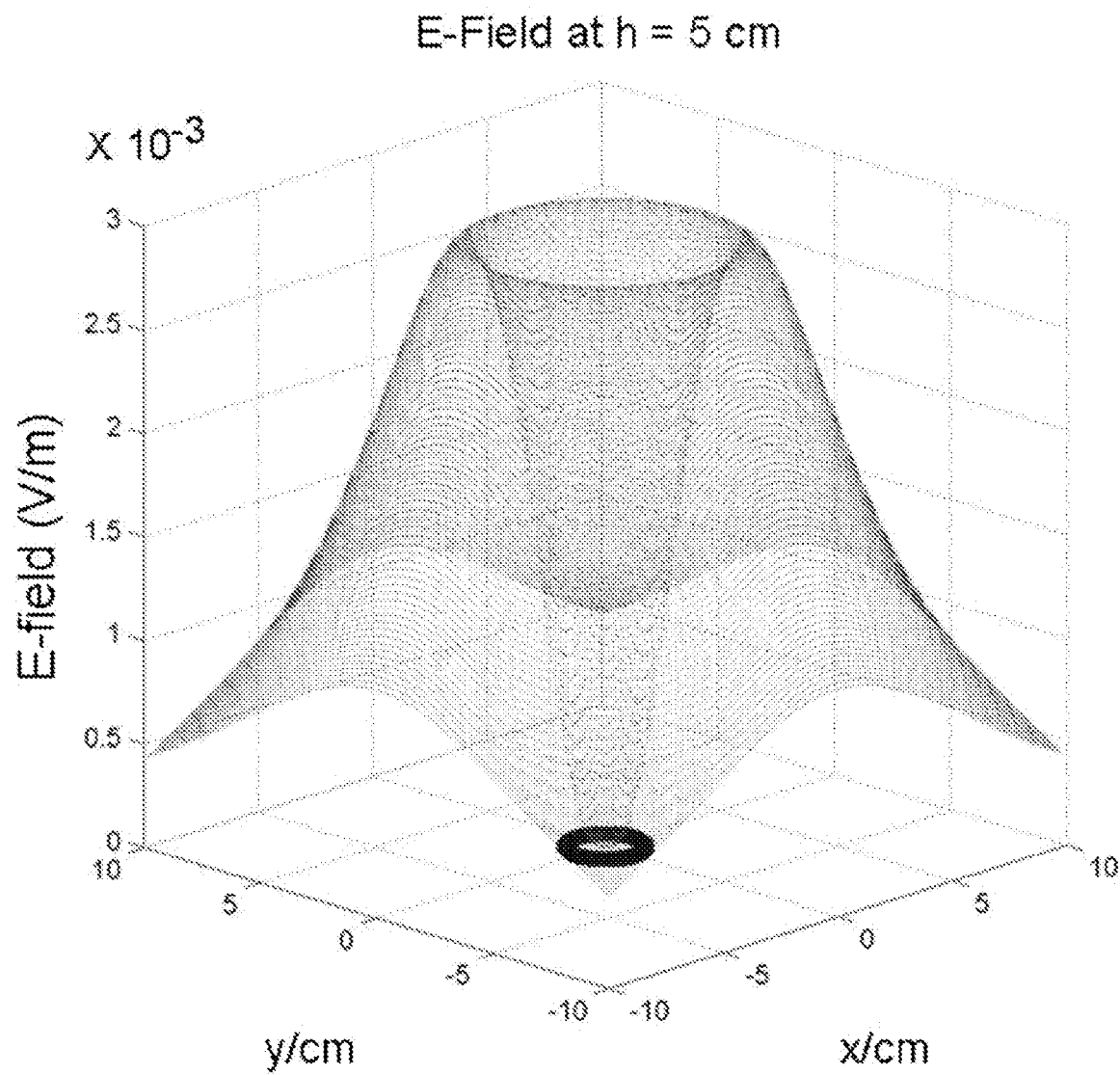
FIG. 2 shows the E-field (red) induced by a single coil (black) in the distance of 0.5 cm above the coil. The figure reveals the high E-field at the periphery of the coil.
Figure 3:
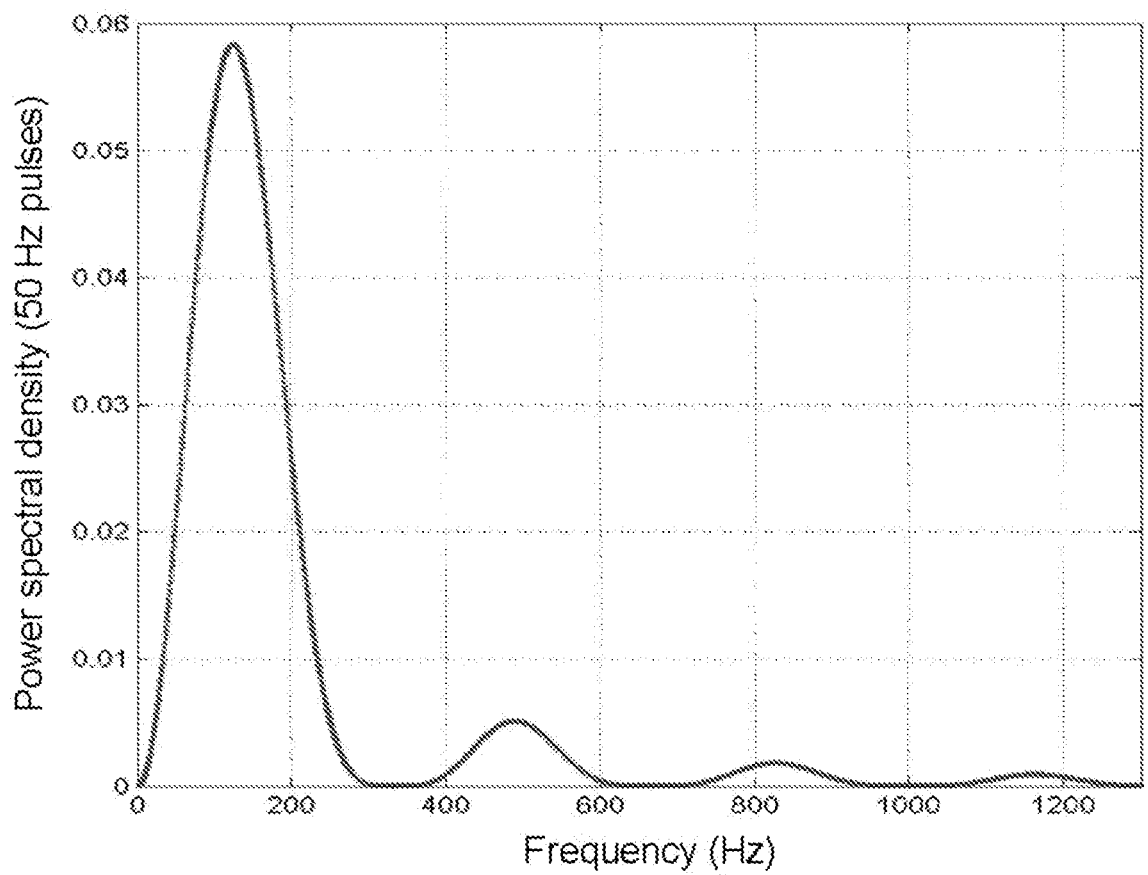
FIG. 3 shows a plot of the power spectral density function, which is found by Fourier transforming the square wave function from the pulse generator.

The E-field induced by a single coil (black) in the distance of 5 cm from the coil is $10^{-3}$ V/m. above the coil was calculated (see FIG. 2). It is evident that the strongest induced E-field is present in the periphery of the coils consistent with measurements and calculations described in U.S. Pat. No. 6,561,968 and EP 1216076. The most prominent frequencies as determined by Fourier analysis of the magnetic field strength measured around the coils are shown in FIG. 3. A pulse configuration as that provided by the pulse generator gives rise to a relative broad band of frequencies. The highest frequencies in the main peak obtained when applying 50 Hz pulse trains are ~333 Hz. The power spectral density function for the square wave function results from the bipolar pulses from the pulse generator. A range of lower frequencies is also produced due to the continuous generation of bipolar pulses from the pulse generator. As seen from the figure, the frequency composition of the square wave function is located primarily below 333 Hz, with a peak maximum at ~150 Hz. This peak maximum is to be expected since each bipolar pulse from the pulse generator gives rise to three separate peaks in the induced electrical field as can be seen from FIG. 1B.

Surprisingly, this particular power spectrum can cause protein activation in the signalling pathway associated with receptor tyrosin kinases and consequently protein kinase activity, mRNA synthesis and biological activity.

Figure 4:
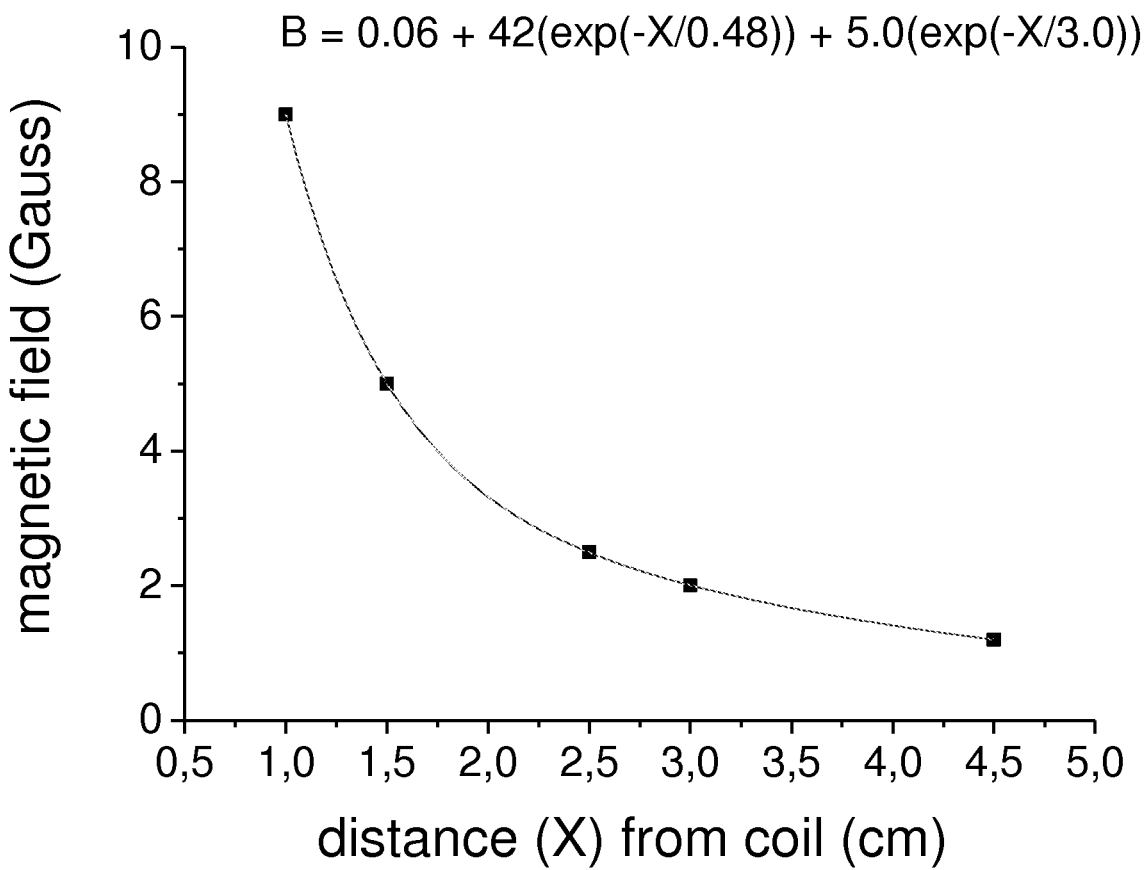
FIG. 4 shows changes in magnetic field density as function of distance from coil. B indicates magnetic field (Gauss) and X distance from coil. At the periphery of the coil it can be calculated that maximum field strength is 42 Gauss and decreases with distance according to the equation is: $B = Y1 + A1(\exp(-X/t1)) + A2(\exp(-X/t2))$, where B is the magnetic field, x is distance and A1, A2, Y1, are constants.

The maximum induced magnetic field and thereby the maximum induced electrical field decreases with distance from the coil as shown in FIG. 4. Magnetic field intensity was measured with a Gauss meter and plotted as a function of distance. This measurement reveals the extent to which the induced electrical field will decrease with distance from the coil.

Figure 5:
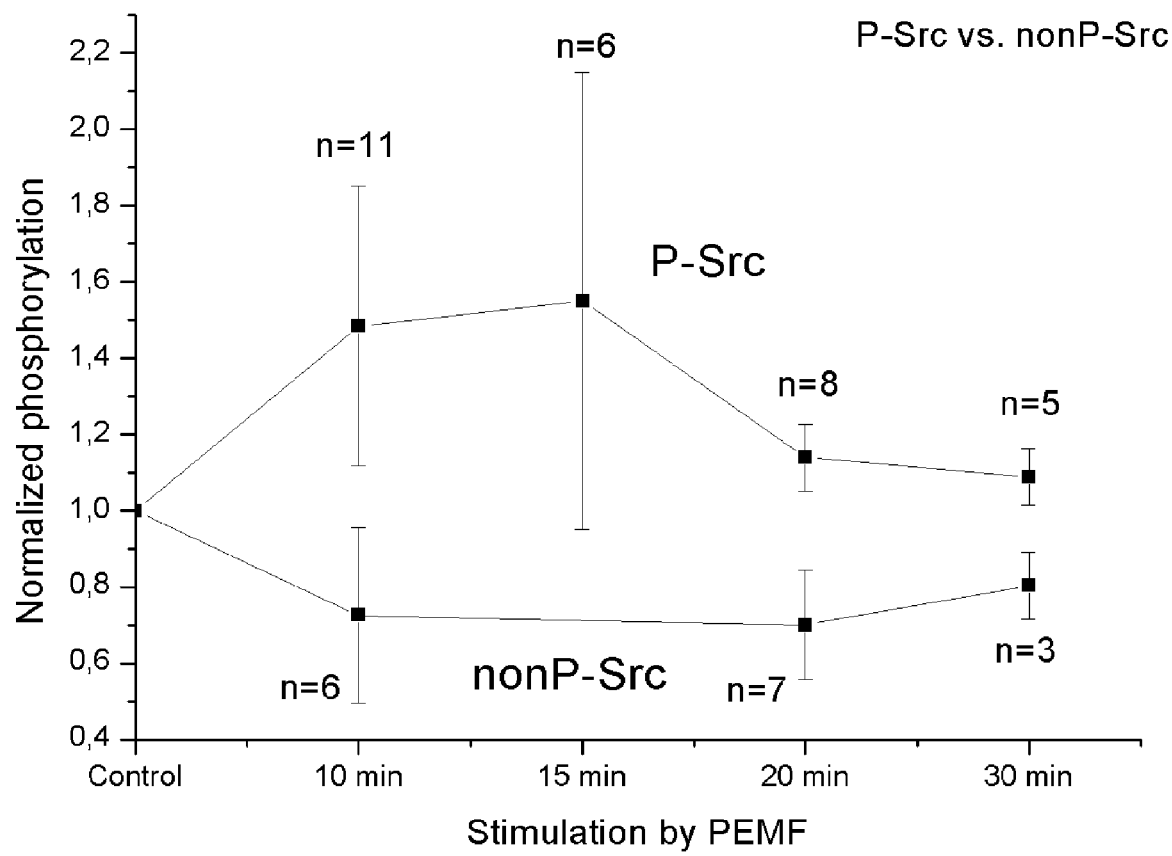
FIG. 5 shows changes in phosphorylation pattern of the Src protein in endothelial cells following exposure to PEMF at 37° C. in a medium containing physiological salt concentrations (RPMI 1640) with 5% fetal calf serum. The phosphorylation pattern of the activation site (Tyr 416) and the inactivation site (Tyr527) were measured using western blotting technique. It is shown that the phosphorylation at 416 and dephosphorylation at 527, both consistent with protein activation, occur between 5, 10 and 30 min.

The biological sensor for PEMF in most cells types is the Src protein that links receptor tyrosin kinase receptors and receptors for cytokines and interleukines to the intracellular signaling cascades causing initiation of mitogen activated protein kinases (MAPK) and thereby transcription. (Rahbek et al., 2005). The protein consists of subunits that can be phosphorylated and these processes are essential for the protein activation. The inventors therefore investigated the time dependency of these phosphorylation processes following cell stimulation. Through western blot analysis the inventors measured the phosphorylation level of the two major phosphorylation sites on the Src protein; Tyr416 located in the activation loop of the kinase, the phosphorylation of which implies Src activation, and the Tyr527 located in the regulatory tail of the kinase, the dephosphorylation of which causes an unfolding of the Src protein, an event resulting in an increased kinase activity. FIG. 5 show that changes in phosphorylation pattern necessary for protein activation occur between 10 and 30 min and similar data were also obtained measuring the phospholipase γ protein that is also linked to the receptor tyrosin kinase as well as other receptors. These data indicates that a significant number of pulses over 10-30 min may be necessary for obtaining the desired biological effect.

Figure 6:
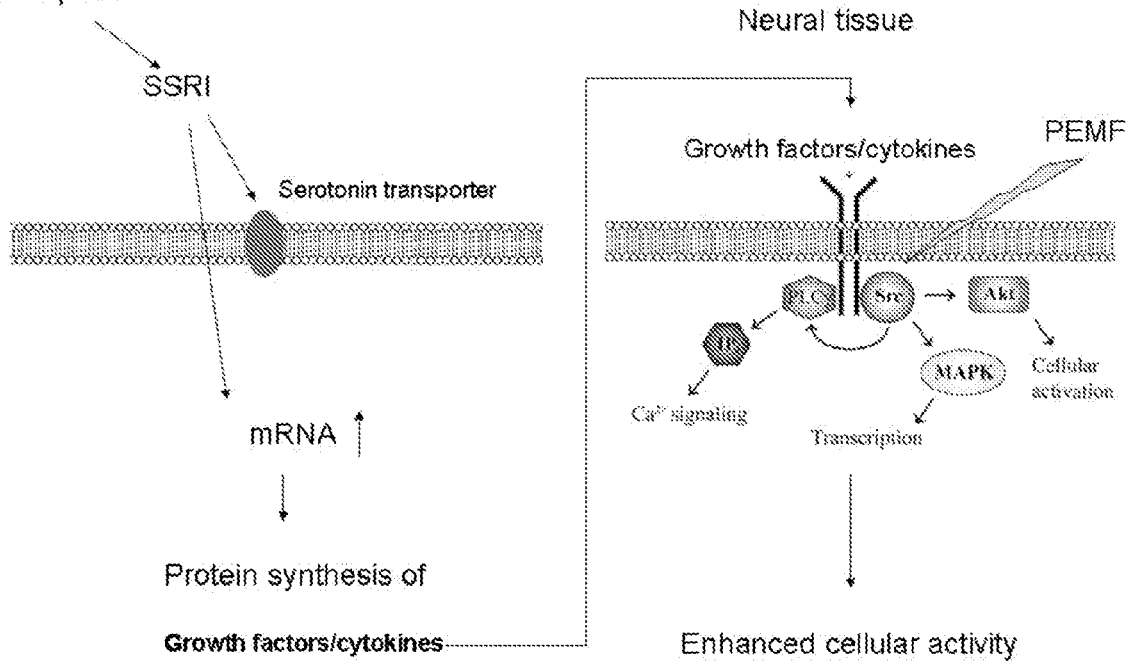
FIG. 6 shows a model depicting the facilitation by PEMF of release of cytokines and growth factors from nerve cells and endothelial cells. SSRI can by itself promote mRNA synthesis of a number of activating factors. Add on effect of PEMF causes an increased cell activation with the Src protein being the sensor for the pulsed electrical fields. (Time dependency for the process is seen in FIG. 5). The result is further cell activation with enhanced cell activity, enhanced blood flow, angiogenesis and consequently beneficial clinical effects.
Figure 7:
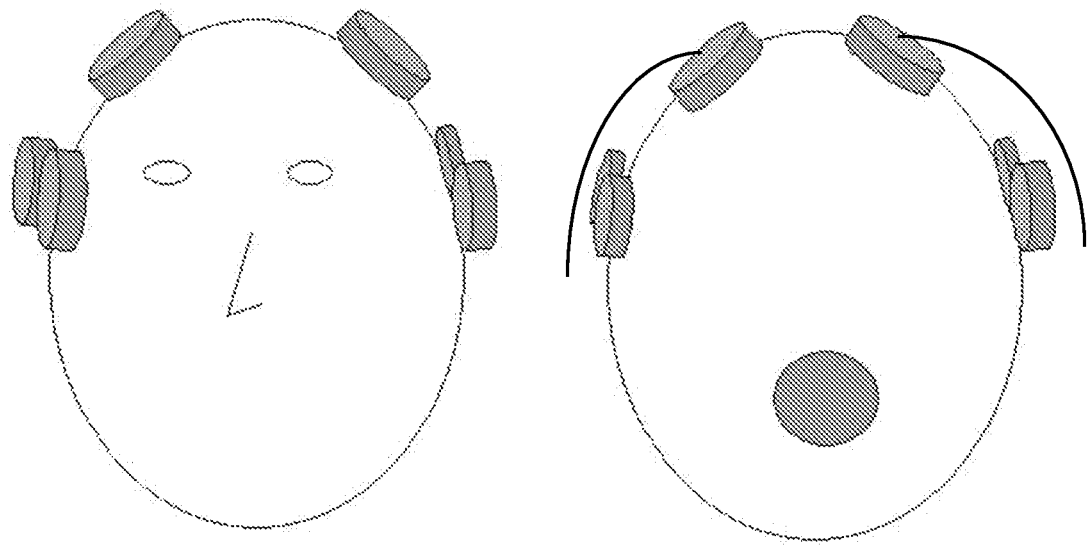
FIG. 7 depicts a preferred positioning of seven coils according to the invention.

The biological effects on the brain are due to an enhanced plasticity of the neural tissue. Without being bound by theory the present inventors suggest that the enhancement in plasticity is due to the PEMF-induced Src activation, MAPK activation and in turn mRNA synthesis and in turn protein synthesis (see model FIG. 6) releasing growth factors, such as brain derived neurotrophic factor (BNDF) and fibroblast growth factor, and angiogenic factors, such as IL-8 and IL-20, to the surroundings. This causes an enhanced blood flow and activation of neural tissue. It is a process that supports and enhances reuptake inhibitors of nor-adrenaline and serotonin that also causes an enhanced activity of neural tissue. An embodiment of the invention concerns an apparatus, adapted to provide a series of pulses consisting of 5000-5,000,000; more preferred 10,000-1,000,000; preferably 50,000-500,000; more preferred 100,000-300,000 pulses.

Pulsed electromagnetic fields have been shown to activate cellular mechanisms that are responsible for activating cellular signaling pathways from receptor tyrosine kinases such as the nerve growth factor family including BDNF as well as FGF receptors and VEGF receptors. Thus PEMF imposed on capillary endothelial cells or neural cells can facilitate or accelerate processes linked to receptor tyrosine kinase functions, that is, synthesis of growth factors as well as release of growth factors that in turn after entering the blood and interstitial fluid can stimulate in a paracrine fashion neighboring cells. Thereby, PEMF stimulation of brain tissue in living human beings could possibly improve neural function. That is, improve pathological conditions such as above mentioned disorders (for a model see FIG. 6). The interesting and newly discovered feature about these activation processes is that they need a considerable number of pulses, preferably administered over 30 min, to activate the biochemical processes. Therefore in this invention the inventors constructed an apparatus that provides such pulses without harmful effects on the tissue/person treated and causing an accumulated protein-activating effect. In order for such a device to be efficient it is then preferable to use many pulses over a period of time without causing side effects on the tissue treated.

The number of pulses that are necessary for the desired effect can be calculated from FIG. 5 in which it can be seen, as well as from other data obtained, that about 10 min stimulation appears to be necessary for the effect and that preferably 30 min stimulation should be applied in the 50 Hz pulse application. A 30 min application with the most frequent pulse pattern occurring at 150 Hz provides a total number of induced electric pulses of 300,000.

Pulsed electrical fields may be used for activating biochemical signalling in both capillary endothelial cells and neural cells whereby growth factors are synthesised intracellularly and released to either the interstitial fluid or the blood circulation. Thereby neural cells become activated by these stimulating agents. The action on PEMF on the Src tyrosine kinase or other tyrosine kinases provides the link between PEMF and biological activity. A new discovery according to this invention is that the number of pulses at this particular field intensity has to be large in order for protein structures to be activated that are dependent on pulsating electrical fields. In addition, this invention may according to an embodiment be a portable conveniently sized apparatus that can be easily transported by the patient. Finally, the present apparatus may be constructed with its coil design and pulse pattern in such a way that an E-field strength >about 30 μV/cm are easily induced up to 10 cm from the coils.

An embodiment of the invention concerns an apparatus, adapted to provide pulsed magnetic fields having a maximum magnitude of 0.1-500, preferably 0.5-250, more preferred 1-100, preferably 5-50, more preferred about 10 mT.

An embodiment of the invention concerns an apparatus, wherein said maximum field strength falls in the interval 0.02-2.0, preferably 0.05-1.0, more preferred 0.1-0.5, preferably 0.15-0.25, more preferred about 0.2 V/m at a distance of 1 cm from each coil.

An embodiment of the invention concerns an apparatus, wherein said maximum field strength falls in the interval $1 \times 10^{-6}$-0.1; more preferred $2 \times 10^{-6}$-0.05; preferably $5 \times 10^{-6}$-0.01; more preferred $10 \times 10^{-6}$-0.005; preferably $50 \times 10^{-6}$-$1 \times 10^{-3}$; more preferred $30 \times 10^{-6}$-$0.5 \times 10^{-6}$; preferably $25 \times 10^{-6}$-$100 \times 10^{-6}$; more preferred $20 \times 10^{-6}$-$50 \times 10^{-6}$; preferably $15 \times 10^{-6}$-$30 \times 10^{-6}$ V/m at a distance of 10 cm from each coil.

Suitable current pulses may, depending on the material and geometry of the coil(s), typically have a maximum current of 10-1000, preferably 20-500, more preferred 50-200, preferably about 100 mA. The typical maximum voltage is 5-500, preferably 10-200, more preferred 30-100, preferably 50 V.

If the potential difference is 70 mV between cytoplasm and extracellular fluid in a cell and the membrane thickness is 100 Å, the potential difference amounts to 70 mV/$10^{-8}$ M=7 $10^6$ V/m. Using the above described TMS technology that imposes potential differences across nerve cell membranes that are close to the level that elicits action potential, it can be assumed that depolarisation of 35 mV is introduced across the membrane. That is sufficient to open the voltage dependent Na$^+$ channels. That depolarisation corresponds to 1.5 $10^6$ V/m. In contrast, the present invention preferably induces an E-field across biological tissue that amounts to about 0.5 V/m. That is, about 6 orders of magnitude less than the depolarisation introduced by the TMS technology. However, other less preferred E-fields may be applied.

The induced biological activity by PEMF using the described technology is effect full in the range of 0-10 cm. This construction is based on knowledge of E-field intensity and decrease in magnetic field with distance. Thus, the assessment is based on the calculations and measurements of the decrease in magnetic field strength (and thus dB/dt) as a function of distance from coil. The magnetic field strength decreases with a factor approximately equal to the distance squared. Therefore, the induced electrical field gradient is significantly decreased even a few cm from the coils, as also indicated in U.S. Pat. No. 6,561,968. In FIG. 4, the decrease in magnetic field strength as a function of the distance from coil surface has been measured. A double exponential has been used to obtain a curve fit for the data. From this fit we can according to the relationship (see equation in the figure) calculate that at a distance of 10 cm the B value has decreased to 0.24 Gauss. At 0.5 cm from the coil the B field is calculated to 19 Gauss by use of the equation. Thus, the field strength has decreased (19/0.25) by a factor of 76 when one is moving from 0.5 cm from coil surface to 10 cm from coil surface. The expected induced E-field will accordingly decrease from about 2.2 mV/cm to appr. 0.030 mV/cm or 30 pV/cm. This value is well above the lower limit of E-fields for inducing biological effects. From Ruben et al. (1993) it is stated:

"In summary, these data suggest that maximum electric field efficacy will be achieved if the signal is confined to a frequency window between 10 Hz and 100 Hz. The sensitivity of the bone cell-matrix composite is such that fields as low as 1 µV/cm will influence bone mass". It is outlined that effect of treatment can be observed at electrical fields as small as $0.1 \times 10^{-3}$ V/m.

Thus, the present apparatus may induce biological effects 10 cm from coil surface with induced E-field of 30 µV/cm when the pulse pattern with its rise time and current density is applied as described.

An embodiment of the invention concerns an apparatus, where the current pulses are supplied with a frequency of preferably 20-300, more preferred 25-200, preferably 50-100 Hz.

Preferably the frequency is preferably above 20 Hz, more preferred above 50 Hz. It is preferred the frequency is below 1000 Hz, more preferred below 500 Hz, preferably below 400 Hz.

An embodiment of the invention concerns an apparatus, where the current pulses are bipolar pulse pairs.

Pulse generator preferably generates bipolar voltage pulse pairs, while other pulse forms may be applied. The pulse generator preferably generates square form waves, however, other wave forms may be applied.

An embodiment of the invention concerns an apparatus, where the current pulses have a duration of 0.1-20, preferably 0.5-10, more preferred 1-5, preferably 2-4, more preferred 3 ms.

An embodiment of the invention concerns an apparatus, where the time between each new current pulse is 5-100, preferably 10-50, more preferred 15-20, preferably 18 ms.

An embodiment of the invention concerns an apparatus, where the delay between pulse pairs is 1-50, preferably 5-25, more preferred 10-15, preferably 12 ms.

An embodiment of the invention concerns an apparatus, wherein at least two, adjacent coils, such as nearest neighbours, are oppositely polarized. This positioning of the coils provides a larger magnetic field while maintaining a lower voltage and hence current level in the coils as described in U.S. Pat. No. 6,561,968.

An embodiment of the invention concerns an apparatus, comprising at least two paired coils having a bitemporal placement adjacent to hippocampus.

An embodiment of the invention concerns an apparatus, wherein at least one coil is positioned near the frontal lobes, allowing stimulation of the frontal lobes.

An embodiment of the invention concerns an apparatus, wherein at least two coils are positioned at each side of the head, near the frontal lobes, allowing stimulation of the frontal lobes.

An embodiment of the invention concerns an apparatus, wherein at least two coils are positioned symmetrically at each side of the head, allowing stimulation of the frontal lobes.

An embodiment of the invention concerns an apparatus, comprising two single paired coils having a parietal placement.

An embodiment of the invention concerns an apparatus, wherein at least one coil has an occipital placement.

An embodiment of the invention concerns an apparatus, further comprising means for holding said at least one coil in the desired position with respect to the tissue to be stimulated.

An aspect of the invention concerns a kit, comprising an apparatus according to the invention, accompanied by instructions to use said apparatus for the treatment of depression, preferably in combination with a pharmaceutical for the treatment of depression.

An aspect of the invention concerns the use of a pulsed electromagnetic field applied trans-cranially to the hippocampus of a subject for the treatment or prophylaxis of a condition selected from the group consisting of depression, major depressive disorder, bipolar disorder/manio depression, epilepsy, Parkinson's disease and Alzheimer's disease and/or for alleviating one or more symptoms associated with said condition.

An embodiment of the invention concerns a use, wherein said pulsed magnetic field applied to the bitemporal area adjacent to the hippocampus is combined with a pulsed magnetic field applied trans-cranially to occipital area.

An embodiment of the invention concerns a use, wherein said electromagnetic field applied to the hippocampus and optionally to the cerebellum and/or the frontal lobes is applied at a current pulse frequency as specified above.

An embodiment of the invention concerns a use, wherein said pulsed electromagnetic field applied to the hippocampus and optionally to the cerebellum and/or the frontal lobes is applied for a period of 5-120, 10-90, preferably 15-60, more preferred 20-40, preferably about 30 minutes.

An embodiment of the invention concerns a use, wherein said pulsed electromagnetic field applied to the hippocampus and optionally to the cerebellum and/or the frontal lobes is applied on a daily basis, every second day, or every third day.

An embodiment of the invention concerns a use, wherein said pulsed electromagnetic field applied to the hippocampus and optionally to the parietal area and/or the occipital area is applied on a daily basis, every second day, or every third day.

An embodiment of the invention concerns a use, wherein the total number of pulses in an administered series is as noted above.

An embodiment of the invention concerns a use, wherein said pulsed electromagnetic field applied to the hippocampus and optionally to the cerebellum and/or the frontal lobes results from current pulses subject to at least one proviso as mentioned above.

An embodiment of the invention concerns a use, wherein said pulsed magnetic field when applied to confluent in vitro cultures of human dermal microvascular endothelial cells as described herein is capable of:

i) increasing the levels of mRNA coding for colony stimulating factor I (CSF1), growth differentiation factor 11 (GDF11) and/or Interleukin 14 (IL-14) by a factor of at least 10;
  ii) increasing the levels of mRNA coding for Platelet derived growth factor AA (PDGF-AA), Transforming growth factor 1 (FGF1), Transforming growth factor 3 (TGF3), Lymphotoxic peptide (Lta) and/or Transforming growth factor alpha (Tgfa) by a factor of at least 4;
  iii) increasing the levels of mRNA coding for Fibroblast growth factor receptor (FGFR) by a factor of at least 0.5; and/or
  iv) increasing the levels of mRNA coding for Brain Derived neurotrophic factor (BNDF) by a factor of at least 1.3 and/or increasing the levels of mRNA coding for Fibroblast Growth Factor (FGF) by a factor of at least 1.2.

An embodiment of the invention concerns a use, wherein said pulsed magnetic field when applied to confluent in vitro cultures of human neural cells SH-SY5Y as described herein is capable of:
i. increasing the levels of mRNA coding for bone morphogenic protein 1 (BMP1), Interleukin 18 (IL-18), Interleukin 20 (IL-20) and/or interleukin 21 (IL-21) by a factor of at least 2;
ii. increasing production of mRNA coding for interleukin 17B (IL-17B), interleukin 8 (IL-8), tumor necrosis factor (TGF), tumor necrosis factor receptor SF11 (TNFR SF11), tumor necrosis factor SF10 (TNF SF10) and/or bone morphogenenic protein 5 (BMP5) by a factor of at least 4;
iii. increasing the production of mRNA coding for interleukin 10 (IL-10), and/or tumor necrosis factor (TNF SF11) by a factor of at least 0.5; and/or
iv. increasing the levels of mRNA coding for Brain Derived neurotrophic factor (BNDF) by a factor of at least 1.3, and of a factor of at least 2 in the presence of 10 μM sertraline.

An embodiment of the invention concerns a use, wherein said subject has a Hamilton depression scale (HAM-D17) of 13 or more before onset of treatment.

In order to activate the relevant neural tissue in the brain correct placement of the coils is important. In a preferred embodiment two pairs of coils are placed over the hippocampus area in such a way the generated electrical fields from opposite coils support each other, similar to the respective arrangement described in U.S. Pat. No. 6,561,968 and EP 1216076. In addition two coils are placed over cortex and one coil in the posterior area.

Another aspect of the invention relates to the use of an antidepressant substance or compound for the manufacture of a medicament for preventing, treating or relieving depression a disorder selected from the group consisting of Depression, Major Depressive Disorder, Bipolar Disorder, Epilepsy, Parkinson's Disease and Alzheimer's Disease in a subject and/or for alleviating one or more symptoms associated with said disease, said subject receiving treatment by application of a pulsed electromagnetic field trans-cranially to the hippocampus and optionally to the cerebellum and/or the frontal lobes.

The pulsed electromagnetic field applied to the hippocampus and optionally to the cerebellum and/or the frontal lobes may in particular provide a maximum field strength in the interval $1\times10^{-6}$-0.1; more preferred $2\times10^{-6}$-0.05; preferably $5\times10^{-6}$-0.01; more preferred $10\times10^{-6}$-0.005; preferably $50\times10^{-6}$-$1\times10^{-3}$; more preferred $30\times10^{-6}$-$0.5\times10^{-6}$; preferably $25\times10^{-6}$-$100\times10^{-6}$; more preferred $20\times10^{-6}$-$50\times10^{-6}$; preferably $15\times10^{-6}$-$30\times10^{-6}$ V/m at a distance of 10 cm from each coil.

In further embodiments said maximum field strength falls in the interval 0.02-2.0, preferably 0.05-1.0, more preferred 0.1-0.5, preferably 0.15-0.25, more preferred about 0.2 V/m at a distance of 1 cm from each coil.

In particular embodiments, said electromagnetic field applied to the hippocampus and optionally to the cerebellum and/or the frontal lobes is applied with a current pulse frequency of 3-1000, preferably 5-500, more preferred 10-400, preferably 20-300, more preferred 25-200, preferably 50-100 Hz, most preferred 50-60 Hz.

The pulsed electromagnetic field may be applied to the hippocampus and optionally to the cerebellum and/or the frontal lobes for a period of 5-120, 10-90, preferably 15-60, more preferred 20-40, preferably about 30 minutes.

According to need, the pulsed electromagnetic field applied to the hippocampus and optionally to the cerebellum and/or the frontal lobes may be applied several times a day, such as 2, 3, 4 or 5 times a day, on a daily basis, every second day, or every third day.

The total number of pulses in an administered series may be 5000-5,000,000; such as 10,000-1,000,000; such as 50,000-500,000; or such as 100,000-300,000 pulses.

In particular embodiments, said subject receives treatment with an apparatus for stimulating brain tissue with pulsed electromagnetic fields weaker than the limit for elicitation of the action potentials of the cells of the tissue to be stimulated.

The apparatus may comprise:
at least one electrically conducting coil at a bitemporal position such that hippocampus is stimulated by at least one magnetic field upon supplying a pulse to said coil; and
a pulse generation means operationally connected to said at least one coil for supplying a series of current pulses for conduction, allowing generation of pulsed magnetic fields sufficiently strong to cause protein activation, and weaker than the limit for elicitation of the action potentials of the cells of the tissue to be stimulated.

In further embodiments said apparatus is an apparatus having the features as described hereinabove.

The use of the apparatus may naturally be combined with other types of treatment for depression, such as noradrenergic and specific serotonergic antidepressants (NaSSA), including Mirtazapine ((±)-1,2,3,4,10,14b-hexahydro-2-[11C]methylpyrazino(2,1-a)pyrido(2,3-c)(2)benzazepine); tetracyclic antidepressants, including Mianserin ((±)-2-methyl-1,2,3,4,10,14b-hexahydrodibenzo[c,f]pyrazino[1,2-a]azepine); tricyclic antidepressants (TCAs), including Amitriptyline (3-(10,11-dihydro-5H-dibenzo[[a,d]]cycloheptene-5-ylidene)-N,N-dimethyl-1-propanamine) and Nortriptyline (3-(10,11-dihydro-5H-dibenzo[a,d]cyclohepten-5-ylidene)-N-methyl-1-propanamine); noradrenaline reuptake inhibitors (NaRI), including Reboxetine ((R*,R*)-2-[(2-ethoxyphenoxy)-phenyl-methyl]morpholine); monoamine oxidase inhibitors, including Isocarboxazid (N'-benzyl-5-methylisoxazole-3-carbohydrazide); mood stabilizers, including Lithium, Lamotrigine (6-(2,3-dichlorophenyl)-1,2,4-triazine-3,5-diamine), Valproic acid (2-propylpentanoic acid) and Topiramate (2,3:4,5-Bis-O-(1-methylethylidene)-beta-D-fructopyranose sulfamate); antipsycotics, including Olanzapine (2-methyl-4-(4-methyl-1-piperazinyl)-10H-thieno[2,3-][1,5]benzodiazepine), Chlorprothixene ((Z)-3-(2-chlorothioxanthen-9-ylidene)-N,N-dimethyl-propan-1-amine) and Quetiapine (2-(2-(4-dibenzo[b,f][1,4]thiazepine-11-yl-1-piperazinyl)ethoxy)ethanol); benzodiazepines, including Oxazepam ((RS)-9-chloro-4-hydroxy-6-phenyl-2,5-diazabicyclo[5.4.0]undeca-5,8,10,12-tetraen-3-one), Alprazolam (8-chloro-1-methyl-6-phenyl-4H-[1,2,4]triazolo[4,3-a][1,4]benzodiazepine) and Lorazepam ((RS)-9-chloro-6-(2-chlorophenyl)-4-hydroxy-2,5-diazabicyclo [5.4.0]undeca-5,8,10,12-tetraen-3-one); hypnotics, including Zolpidem (N,N,6-Trimethyl-2-(4-methylphenyl)-imidazo[1,2-a]pyridine-3-acetamide) and Zopiclone ((RS)-[8-(5-chloropyridin-2-yl)-7-oxo-2,5,8-triazabicyclo[4.3.0] nona-1,3,5-trien-9-yl]-4-methylpiperazine-1-carboxylate); and 5-HT-prodrugs, or combinations of any of these.

It appears that the new generation of antidepressants (SSRIs) have dual actions. Besides inhibiting the reuptake of serotonin thereby affecting the activity of the facilitated serotonin transport and causing an increased serotonin activity in the synaptic cleft, the consequences are that intracellular signalling is affected. For a model of interactions see FIG. 6. The action of the SSRI causes an enhanced mRNA synthesis for growth factors such as brain derived neurothrophic factor (Kozisek et al., 2008) and FGF. Kozisek et al. (2008) emphasize that "results from clinical and basic studies have demonstrated that stress and depression decrease BDNF expression and neurogenesis and antidepressant treatment reverses or blocks these effects, leading to the neurotrophic hypothesis of depression. Clinical studies demonstrate an association between BDNF levels and several disorders, including depression, epilepsy, bipolar disorder, Parkinson's and Alzheimer's diseases".

In a study on human patients with major depressive disorders (MDD), Evans et al (2004) have shown that, through a separate analysis of specific serotonin reuptake inhibitor (SSRI)-treated and non-SSRI-treated MDD subjects that the observed changes in expression of FGF transcripts are not secondary to drug treatment. They find that changes in specific FGF transcripts are attenuated by SSRIs and may thus be partially responsible for the mechanism of action of these drugs. It has also been emphasized that electroconvulsive seizure (ECS) causes a more than 2 fold increase in mRNA for BDNF. Similar findings from other groups have shown that there was a trend towards increased BDNF expression in hilar and supragranular regions in depressed subjects treated with antidepressants, compared with subjects not on this medication. In the study shown here it was also found that the human neuroblastoma cell line SH-SY5Y contains BDNF and appears to be a well suited model for studying the regulation of mRNA for BDNF. This finding has been used in the following to close the link between SSRI effects, PEMF activation, mRNA synthesis and receptor activation. Furthermore, it has been shown that following mental depression there is a loss of hippocampus volume and a diminished blood flow. Improvement in this anatomical and physiological condition is essential for improving the pathological state.

Surprisingly, the combination of SSRI and PEMF together facilitates or magnifies the biological effect of both components. It has not been previously anticipated that combining PEMF with SSRI will yield a dramatic upregulation of mRNA for growth factors and consequently their release as described. The consequence is a dramatic enhanced activity due to the growth factor and cytokine release by neurosecretion and thereby improved neural activity as evident from a described clinical investigation.

Serotonin-norepinephrine reuptake inhibitors (SNRIs) are antidepressant drugs used in the treatment of major depression and other mood disorders. SNRIs affect reuptake of both serotonin and norepinephrine. These inhibitors can be seen as a different class compared to the widely-used selective serotonin reuptake inhibitors (SSRIs) shown above. SNRIs can be used in the treatment of major depression and other mood disorders. SNRIs are able to increase the levels of nor-epinephrine and serotonin in the synaptic cleft thereby enhancing cellular activity. Nor-epinephrine acts by increasing cyclic AMP (cAMP) activity in turn by activating MAPK activity. PEMF exposure that activates Src kinase activity will then in concert with the cAMP effects cause a further enhancement of cellular activity.

Hence in further embodiments said antidepressant substance or compound is selected from the group consisting of a serotonin-norepinephrine reuptake inhibitor (SNRIs) and a selective serotonin reuptake inhibitor/serotonin-specific reuptake inhibitor (SSRIs). In particular, said Serotonin-norepinephrine reuptake inhibitor may be selected from the group consisting of Venlafaxine (Effexor) ((RS)-1-[2-dimethylamino-1-(4-methoxyphenyl)-ethyl]cyclohexanol) and Duloxetine (Cymbalta, Yentreve)((+)-(S)—N-Methyl-3-(naphthalen-1-yloxy)-3-(thiophen-2-yl)propan-1-amine).

Preferably, said serotonin reuptake inhibitor/serotonin-specific reuptake inhibitor may be selected from the group consisting of citalopram ((RS)-1-[3-(dimethylamino)propyl]-1-(4-fluorophenyl)-1,3-dihydroisobenzofuran-5-carbonitrile), dapoxetine ((S)—N,N-dimethyl-3-(naphthalen-1-yloxy)-1-phenylpropan-1-amine), escitalopram ((S)-1-[3-(dimethylamino)propyl]-1-(4-fluorophenyl)-1,3-dihydroisobenzofuran-5-carbonitrile), fluoxetine ((±)—N-methyl-3-phenyl-3-[4-(trifluoromethyl)phenoxy]propan-1-amine), fluvoxamine ((E)-5-methoxy-1-[4-(trifluoromethyl)phenyl]pentan-1-one O-2-aminoethyl oxime), paroxetine ((3S,4R)-3-[(2H-1,3-benzodioxol-5-yloxy)methyl]-4-(4-fluorophenyl)piperidine), sertraline ((1S,4S)-4-(3,4-dichlorophenyl)-N-methyl-1,2,3,4-tetrahydronaphthalen-1-amine, and zimelidine (3-(4-bromophenyl)-N,N-dimethyl-3-(pyridin-3-yl)prop-2-en-1-amine).

In embodiments which are presently preferred, the serotonin reuptake inhibitor/serotonin-specific reuptake inhibitor is selected from the group consisting of citalopram, escitalopram, fluoxetine and sertraline.

An embodiment of the invention concerns a use, wherein the depression is resistant to medication given without combination with PEMF activation, such as medication with a serotonin-norepinephrine reuptake inhibitors and/or a selective serotonin reuptake inhibitor/serotonin-specific reuptake inhibitor.

An embodiment of the invention concerns a use, wherein said depression is resistant to medication with one or more serotonin-norepinephrine reuptake inhibitors, preferably one or more of the particular serotonin-norepinephrine reuptake inhibitors as identified above, and/or resistant to medication with one or more selective serotonin reuptake inhibitors/serotonin-specific reuptake inhibitor, preferably one or more of the selective serotonin reuptake inhibitors/serotonin-specific reuptake inhibitors identified above.

It may be preferred that administration of said antidepressant substance or compound is wholly or partly discontinued during said treatment by application of pulsed electromagnetic fields. By "partly discontinued" is meant that the said antidepressant substance is administered to the subject at a lower frequency or at lower dosages during the period in which the subject receives treatment with PEMF as compared to the frequency and/or dosages applied before and/or after the said period.

It is contemplated that subjects who in particular would benefit from treatment according to the present invention would have a Hamilton depression scale (HAM-D17) of 13 or more, such as 14 or more, such as 15 or more, such as 16 or more, 17 or more, 18 or more, 19 or more, or such as 20 or more, before onset of treatment.

A further aspect of the invention pertains to an antidepressant substance or compound for use in prophylaxis, treatment or relief of a disorder selected from the group consisting of Depression, Major Depressive Disorder, Bipolar Disorder, Epilepsy, Parkinson's Disease and Alzheimer's Disease in a subject and/or for alleviating one or more symptoms associated with said disease, concomitant or in connection with treatment of said subject by application of a pulsed electromagnetic field trans-cranially to the hippocampus and optionally to the cerebellum and/or the frontal lobes of said subject.

The pulsed electromagnetic field applied to the hippocampus and optionally to the cerebellum and/or the frontal lobes may in particular provide a maximum field strength in the interval $1 \times 10^{-6}$-0.1; more preferred $2 \times 10^{-6}$-0.05; preferably $5 \times 10^{-6}$-0.01; more preferred $10 \times 10^{-6}$-0.005; preferably $50 \times 10^{-6}$-$1 \times 10^{-3}$; more preferred $30 \times 10^{-6}$-$0.5 \times 10^{-6}$; preferably $25\times10^{-6}$-$100\times10^{-6}$; more preferred $20\times10^{-6}$-$50\times10^{-6}$; preferably $15\times10^{-6}$-$30\times10^{-6}$ V/m at a distance of 10 cm from each coil In further embodiments said maximum field strength falls in the interval 0.02-2.0, preferably 0.05-1.0, more preferred 0.1-0.5, preferably 0.15-0.25, more preferred about 0.2 V/m at a distance of 1 cm from each coil.

In further embodiments said pulsed electromagnetic field applied to the hippocampus and optionally to the cerebellum and/or the frontal lobes is applied with a current pulse frequency of 3-1000, such as 5-500, 10-400, 20-300, 25-200, 50-100 Hz, or such as 50-60 Hz.

The pulsed electromagnetic field applied to the hippocampus and optionally to the cerebellum and/or the frontal lobes may be applied for a period of 5-120, 10-90, preferably 15-60, more preferred 20-40, preferably about 30 minutes. Depending on need in each particular case the pulsed electromagnetic field may be applied to the hippocampus and optionally to the cerebellum and/or the frontal lobes several times a day, such as 2, 3, 4 or 5 times daily, on a daily basis, every second day, or every third day.

The total number of pulses in an administered series may be 5000-5,000,000; more preferred 10,000-1,000,000; preferably 50,000-500,000; more preferred 100,000-300,000 pulses.

Further embodiments provide an antidepressant substance or compound for use as described above, wherein said subject receives treatment with an apparatus for stimulating brain tissue with pulsed electromagnetic fields weaker than the limit for elicitation of the action potentials of the cells of the tissue to be stimulated. In particular said apparatus may comprise:

at least one electrically conducting coil at a bitemporal position such that hippocampus is stimulated by at least one magnetic field upon supplying a pulse to said coil; and a pulse generation means operationally connected to said at least one coil for supplying a series of current pulses for conduction, allowing generation of pulsed magnetic fields sufficiently strong to cause protein activation, and weaker than the limit for elicitation of the action potentials of the cells of the tissue to be stimulated.

It is to be understood that the apparatus may have any of the features and characteristics as described hereinabove.

In preferred embodiments, said antidepressant substance or compound is selected from the group consisting of a serotonin-norepinephrine reuptake inhibitor (SNRIs) and a selective serotonin reuptake inhibitor/serotonin-specific reuptake inhibitor (SSRIs). In particular said Serotonin-norepinephrine reuptake inhibitor may be selected from the group consisting of Venlafaxine (Effexor) and Duloxetine (Cymbalta, Yentreve). Further, said serotonin reuptake inhibitor/serotonin-specific reuptake inhibitor may be selected from the group consisting of citalopram, dapoxetine, escitalopram, fluoxetine, fluvoxamine, paroxetine, sertraline, and zimelidine. In presently preferred embodiments, the serotonin reuptake inhibitor/serotonin-specific reuptake inhibitor is selected from the group consisting of citalopram, escitalopram, fluoxetine and sertraline.

Further embodiments relate to an antidepressant substance or compound for use as provided above, wherein said disorder is resistant to medication. In particular, the disorder may be resistant to medication with one or more serotonin-norepinephrine reuptake inhibitors, preferably one or more serotonin-norepinephrine reuptake inhibitors as identified above, and/or resistant to medication with one or more of the selective serotonin reuptake inhibitors/serotonin-specific reuptake inhibitors, preferably one or more selective serotonin reuptake inhibitors/serotonin-specific reuptake inhibitors as identified above.

Subject to assessment of the possible benefits in each particular case, administration of said antidepressant substance or compound is wholly or partly discontinued during said treatment by application of pulsed electromagnetic fields. The subject receiving antidepressant substance or compound as described above preferably has a Hamilton depression scale (HAM-D17) of 13 or more, such as 14 or more, such as 15 or more, such as 16 or more, 17 or more, 18 or more, 19 or more or such as 20 or more, before onset of treatment.

An aspect of the invention concerns a non-invasive method for the treatment or prophylaxis of a condition selected from the group consisting of depression, Major Depressive Disorder, Bipolar Disorder, Epilepsy, Parkinson's disease and Alzheimer's disease and/or for alleviating one or more symptoms associated therewith in a subject, said method comprising a step of applying a pulsed electromagnetic field as set forth in any of the preceding claims trans-cranially to the hippocampus and optionally to the cerebellum and/or the frontal lobes of said subject.

In particular embodiments, said subject receives treatment with an apparatus for stimulating brain tissue with pulsed electromagnetic fields weaker than the limit for elicitation of the action potentials of the cells of the tissue to be stimulated. Preferably, the apparatus is an apparatus as described hereinabove, comprising:

at least one electrically conducting coil at a bitemporal position such that hippocampus is stimulated by at least one magnetic field upon supplying a pulse to said coil; and a pulse generation means operationally connected to said at least one coil for supplying a series of current pulses for conduction, allowing generation of pulsed magnetic fields sufficiently strong to cause protein activation, and weaker than the limit for elicitation of the action potentials of the cells of the tissue to be stimulated.

In further embodiments the method comprises application of an the electromagnetic field to the hippocampus and optionally to the cerebellum and/or the frontal lobes said electromagnetic field providing a maximum field strength in the interval $1\times10^{-6}$-0.1; more preferred $2\times10^{-6}$-0.05; preferably $5\times10^{-6}$-0.01; more preferred $10\times10^{-6}$-0.005; preferably $50\times10^{-6}$-$1\times10^{-3}$; more preferred $30\times10^{-6}$-$0.5\times10^{-6}$; preferably $25\times10^{-6}$-$100\times10^{-6}$; more preferred $20\times10^{-6}$-$50\times10^{-6}$; preferably $15\times10^{-6}$-$30\times10^{-6}$ V/m at a distance of 10 cm from each coil.

In further embodiments said maximum field strength falls in the interval 0.02-2.0, preferably 0.05-1.0, more preferred 0.1-0.5, preferably 0.15-0.25, more preferred about 0.2 V/m at a distance of 1 cm from each coil.

Preferably, said electromagnetic field applied to the hippocampus and optionally to the cerebellum and/or the frontal lobes is applied with a current pulse frequency of 3-1000, such as 5-500, 10-400, 20-300, 25-200, 50-100 Hz, or such as 50-60 Hz.

The pulsed electromagnetic field applied to the hippocampus and optionally to the cerebellum and/or the frontal lobes may be applied for a period of 5-120, 10-90, such as 15-60, such as 20-40, or such as about 30 minutes.

According to need the pulsed electromagnetic field applied to the hippocampus and optionally to the cerebellum and/or the frontal lobes may be applied several times a day, such as 2, 3, 4 or 5 times a day, on a daily basis, every second day, or every third day.

The total number of pulses in an administered series may be 5000-5,000,000; such as 10,000-1,000,000; such as 50,000-500,000; or such as 100,000-300,000 pulses.

Subjects who in particular would benefit from treatment according to the present invention would have a Hamilton depression scale (HAM-D17) of 13 or more, such as 14 or more, such as 15 or more, such as 16 or more, 17 or more, 18 or more, 19 or more or such as 20 or more, before onset of treatment.

The method may further comprise administration to said subject of an antidepressant substance or compound. In preferred embodiments, said antidepressant substance or compound is selected from the group consisting of a serotonin-norepinephrine reuptake inhibitors (SNRIs) and a selective serotonin reuptake inhibitor/serotonin-specific reuptake inhibitors (SSRIs).

Commonly used Serotonin-norepinephrine reuptake inhibitors include Venlafaxine (Effexor) and Duloxetine (Cymbalta, Yentreve). Commonly used serotonin reuptake inhibitor/serotonin-specific reuptake inhibitors include citalopram, dapoxetine, escitalopram, fluoxetine, fluvoxamine, paroxetine, sertraline, and zimelidine.

Preferably, said serotonin reuptake inhibitor/serotonin-specific reuptake inhibitor is selected from the group consisting of citalopram, escitalopram, fluoxetine and sertraline.

In further embodiments the depression is resistant to medication. In particular, depression may be resistant to medication with one or more serotonin-norepinephrine reuptake inhibitors, such as one or more serotonin-norepinephrine reuptake inhibitors as set forth above, and/or resistant to medication with one or more of the selective serotonin reuptake inhibitors/serotonin-specific reuptake inhibitors, such as one or more selective serotonin reuptake inhibitors/serotonin-specific reuptake inhibitors as set forth above.

It is to be understood that subject to evaluation of each particular case administration of said antidepressant substance or compound may be wholly or partly discontinued during said treatment by application of pulsed electromagnetic fields.

Another embodiment concerns a method, further comprising assessing the level of depression in said subject before and after application of said pulsed electromagnetic fields.

All cited references are incorporated in their entirety.

Example 1

Measuring mRNA Synthesis Induced by PEMF from Endothelial Cells and Neural Cells Human dermal microvascular endothelial cells or human neural cells (from sympatic ganglia) SHSY-5Y were grown to confluency in 10 cm petridishes and placed on the coil bed covering the area with a thermostatically controlled (water jacket) bottom. Current for an internal ventilation system in the coil bed as described in U.S. Pat. No. 6,561,968 and EP 1216076. Cells were situated in a cell culture incubator (37° C., 5% $CO_2$) for the time of stimulation, while controls were placed in identical conditions without electromagnetic stimulation. To prevent heat due to the current running in the coils from influencing the cells placed on the coil bed, a water flow cooling device connected to a large thermostatic water reservoir held at 37° C. was placed between the coil bed and the cells. The temperature of the culture medium was measured prior to and during application of PEMF was found to be constant. The pulse generator system used generates bipolar square pulse pairs of ±50V respectively, produced every 18 ms (equivalent to approximately 55 Hz) with a pulse duration of 3 ms as described.

The effects of PEMF on mRNA in endothelial cells was determined using RT-PCR by applying either a PCR array or primers constructed by us and applied on e Statagene Q-PCR machine. The SYBR green fluorescence development was measured on a Stratagene Q-PCR machine. Fold increase was determined from the treshhold set by the program identifying exponential increase of fluorescence and one cycle difference between control and PEMF treated cells was considered a 2 fold increase.

As evident from table I there is a strong enhancement of mRNA coding for growth factors and cytokines in endothelial cells. The significant findings were up regulation of:

1. Transforming growth factor alpha (TGF-α) which is produced in macrophages, brain cells, and keratinocytes, and also here in endothelial cells. It induces epithelial development and is closely related to epidermal growth factor (EGF). TGFα can stimulate neural cell proliferation in the adult injured brain. TGFα was cited in the 2001 NIH Stem Cell report to the U.S. Congress as promising evidence for the ability of adult stem cells to restore function in neurodegenerative disorders.

2. TGFB is a multifunctional peptide that controls proliferation, differentiation, and other functions in many cell types. Dysregulation of TGFB activation and signaling may result in apoptosis. Many cells synthesize TGFB and almost all of them have specific receptors for this peptide.

3. TGF-β1 was first identified in human platelets with a potential role in wound healing. TGF-β1 plays an important role in controlling the immune system, and shows different activities on different types of cell, or cells at different developmental stages. Most immune cells (or leukocytes) secrete TGF-β1.

4. Transforming growth factor beta 3 (TGF-β3) is a type of protein, known as a cytokine, which is involved in cell differentiation, embryogenesis and development. It belongs to a large family of cytokines called the Transforming growth factor beta superfamily, which includes the TGF-β family. TGF-β3 is important for controlling the regulation of cell adhesion and extracellular matrix formation. It controls wound healing by regulating the movements of epidermal and dermal cells in injured skin.

5. FGFR. Receptor for fibroblast growth factor that is a peptide responsible for angiogenesis, wound healing, and embryonic development.

6. LTA. LTA mediates a large variety of inflammatory, immunostimulatory, and antiviral responses. LTA is also involved in the formation of secondary lymphoid organs during development and plays a role in apoptosis.

Human SYSH-5Y cells were incubated in the presence of 10 μM sertraline and 5% FCS in a RPMI medium. Cells all ere treated as described in FIG. 2, and mRNA was measured. It is evident that the combination of SSRI and PEMF gives a strong synthesis of mRNA for a number of growth factors and cytokines (See Table II).

1. The interesting observations are that the IL-10 family that also includes Interleukin-20 (IL-20) which is also upregulated. IL-20 is produced by activated endothelial cells, keratinocytes and monocytes and transmits an intracellular signal through two distinct cell-surface receptor complexes on keratinocytes and other epithelial cells. IL-20 regulates proliferation and differentiation of keratinocytes during inflammation, particularly inflammation associated with the skin. In addition, IL-20 also causes cell expansion of multipotential hematopoietic progenitor cells. Il-20 is also a arteriogenic factor and also a lymphangiogenic factor.

2. Furthermore tumor necrosis factors and receptors are also upregulated. The primary role of TNF is in the regulation of immune cells. TNF is also able to induce apoptotic cell death, to induce inflammation, and to inhibit tumorigenesis and viral replication.

BMP, Bone morphonogenic protein is upregulated. BMPs interact with specific receptors on the cell surface, referred to as bone morphogenetic protein receptors (BMPRs). Signal transduction through BMPRs results in mobilization of members of the SMAD family of proteins. The signalling pathways involving BMPs, BMPRs and Smads are important in the development of the heart, central nervous system, and cartilage, as well as post-natal bone development.

mRNA for BDNF was upregulated by a factor of 1.3 and in the presence with sertraline the effects was enhanced to a final upregulation of a factor of 2. This is observed after 24 hr preincubation with sertraline followed by 2 hrs pulsed electrical fields.

TABLE I

Human dermal microvascular endothelial cells

| Growth factor/cytokine | Abbr. | Fold increase in mRNA after PEMF | PCR method |
|---|---|---|---|
| Colony stimulating factor 1 | CSF1 | 50 | PCR array |
| Growth differentiation 11 | GDF11 | 55 | PCR array |
| Interleukin 14 | IL-14 | 50 | PCR array |
| Platelet derived growth factor AA | PDGFAA | 10 | PCR array |
| Transforming growth factor 1 | TGF1 | 4 | PCR array |
| Transforming growth factor 3 | TGF3 | 14 | PCR array |
| Lymphotoxic peptide | Lta | 4 | PCR array |
| Transforming growth factor alpha | Tgfa | 4 | PCR array |
| Fibroblast growth factor receptor | FGFR | 1.2 | FGF primer (PCR) |

Table I. mRNA was measured in control cells and PEMF activated cells (3 hr, 50 Hz) using a PCR array Common Cytokines (PAHS-021) from Bioscience Corporation, 7320 Exceutive way, Suite 101, Frederick Md., USA.

TABLE II

Human neural cells line from sympatic ganglia - SHSY-5Y

| Growth factor/cytokine | Abbreviation | Fold increase | PCR method |
|---|---|---|---|
| Bone morphonogenic Protein 1 | BMP1 | 4 | PCR array |
| Interleukin 10 | IL-10 | 1 | PCR array |
| | IL-17B | 8 | PCR array |
| | IL-18 | 4 | PCR array |
| | IL-20 | 4 | PCR array |
| | IL-21 | 4 | PCR array |
| | Il-8 | 8 | PCR array |
| Tumor necrosis factor | TNF | 8 | PCR array |
| | TNFR SF11 | 8 | PCR array |
| | TNF SF10 | 8 | PCR array |
| | TNF SF11 | 2 | PCR array |
| Bone morphonogenic Protein 5 | BMP5 | 8 | PCR array |
| Transforming growth factor beta 3 | TGFB3 | 5 | PCR array |
| Brain derived neurotrophis factor | BDNF | 1.3 | Q-PCR |
| Brain derived neurotrophis factor With 10 µM sertraline | BDNF | 2.0 | Q-PCR |

Table II. mRNA was measured in control cells and cells pretreated with the SSRI compound sertraline 10 µM for 24 hours in a 2% fetal calf serum and subsequently PEMF treated for 2 hrs at 50 or 55 Hz. mRNA was measured by using a PCR array Common Cytokines (PAHS-021) from Bioscience Corporation, USA, or by RT-PCR Example 2

The experiments shown in example 1, determining the influence of PEMF on mRNA synthesis in human dermal endothelial cells and in a human neuroblastoma cells, SHSY-5Y, were repeated.

The changes in mRNA expression induced by the PEMF technique were assessed by either RT-PCR with using reverse primer: ATCCAACAGCTCTTCTATCACG and forward primer: CGGAGCAGCTGCCTTGATGG and an annealing temperature of 58° C., or by use of PCR arrays from SA Biosciences 6951 Executive Way, Frederick, Md. 21703 USU according to the manufacturer's instructions. Common cytokines PAHS-021 or TH-17 array PAHS-073 were applied. RNA was isolated and thereafter further DNAase treated also according to the manufacturer and run on a Statagene Q-PCR machine. House hold genes were used as a control and up- and downregulation of genes were calculated using SA Biosciences software (Web side).

Figure 8:
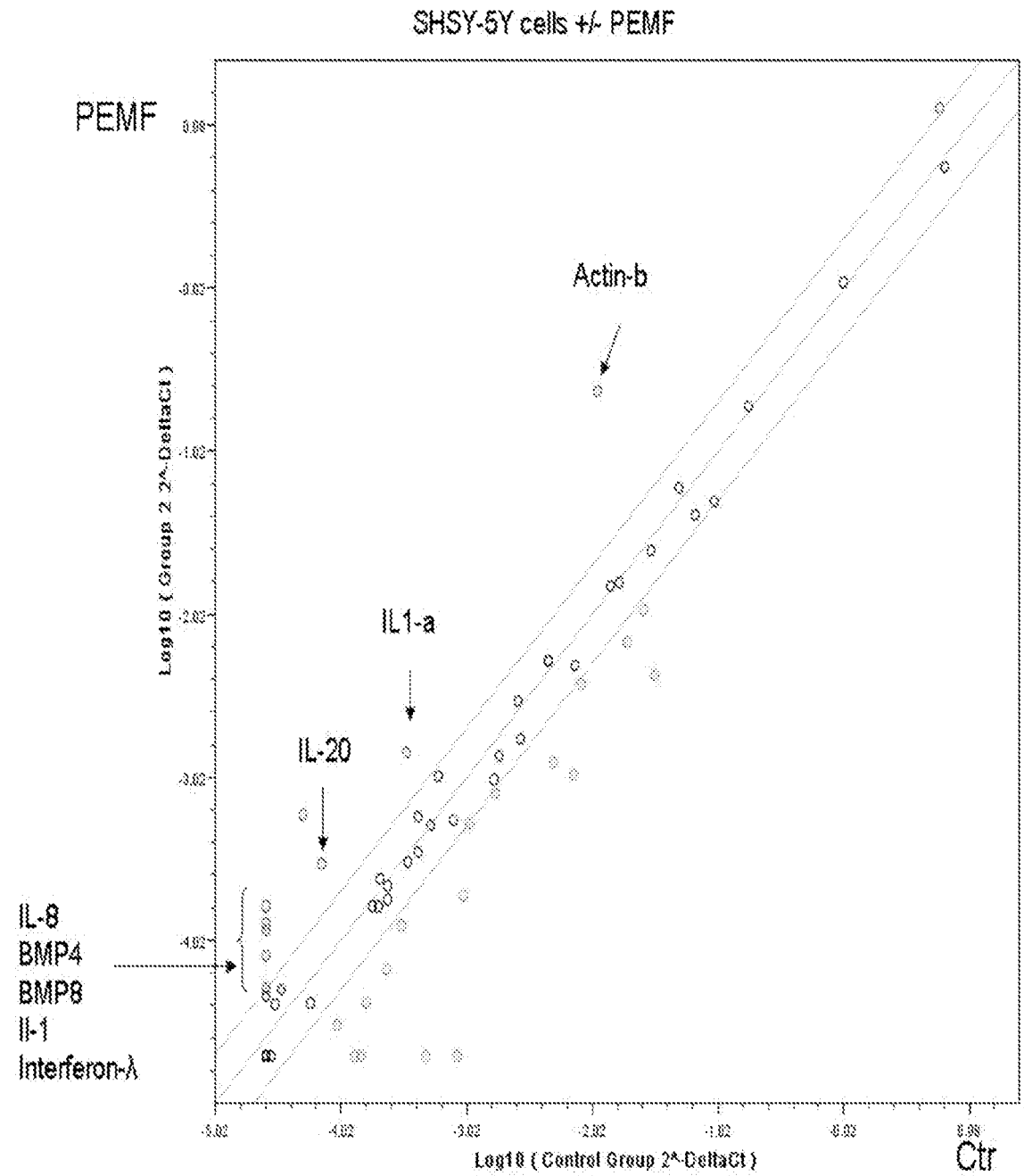
FIG. 8 shows mRNA levels measured in neuroblastoma like cell line SHSY-5Y was treated with PEMF for 2 hrs in 2% growth medium. Measurements were done using PCR array from SA Biosciences (USA). Data following the straight line in the middle is not regulated and mRNA above the solid line (red dots) are upregulated.
Figure 9:
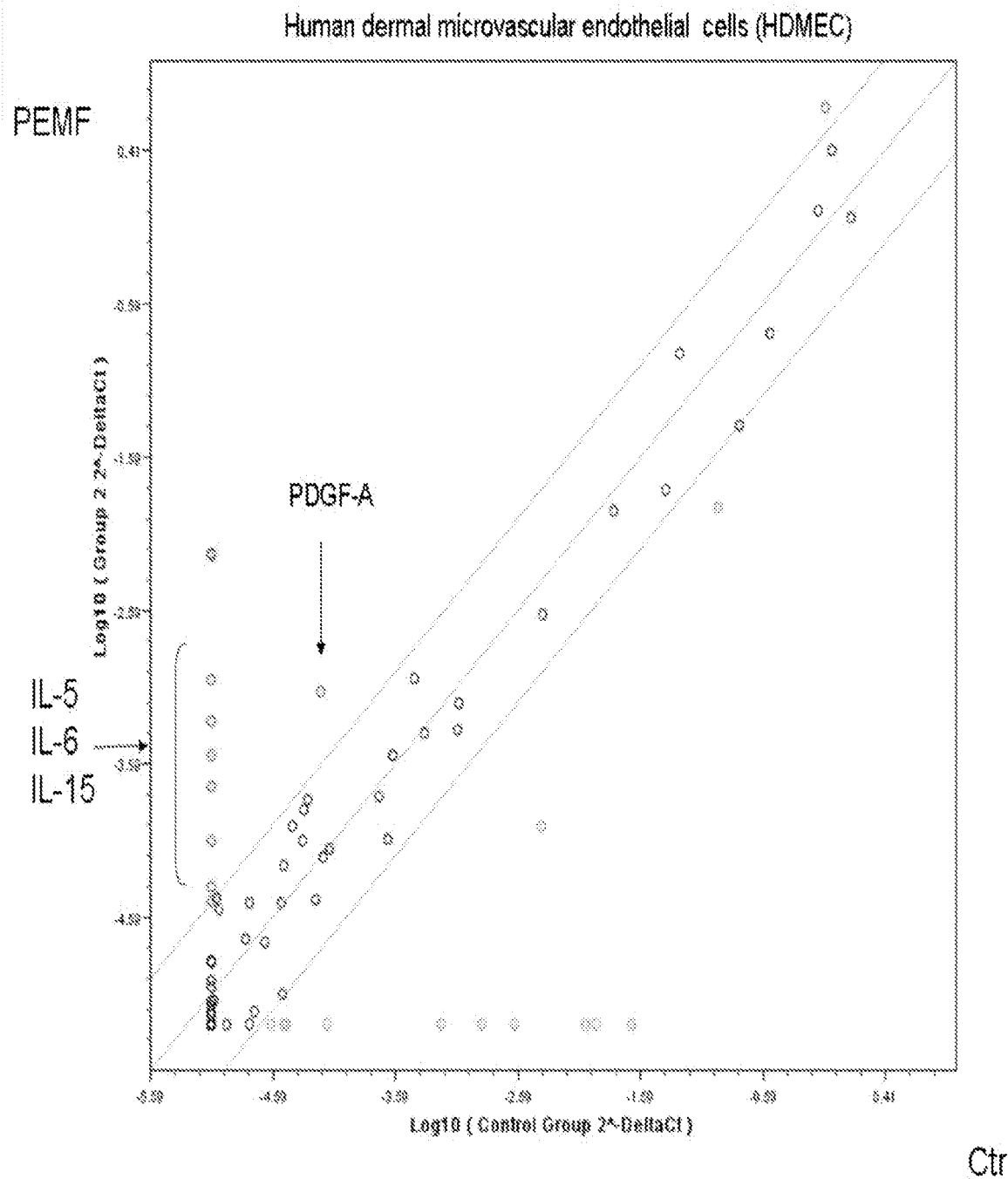
FIG. 9 shows mRNA levels in human dermal microvascular endothelial cells treated with PEMF for 2 hrs. mRNA was measured using the SA Biosciences micro array assay.

Results from measurements of mRNA levels in SHSY-5Y cells treated with PEMF for 2 hrs in 2% growth medium are shown a scatter double log plot in FIG. 8. Results from measurements of mRNA levels in human dermal microvascular endothelial cells treated with PEMF for 2 hrs are shown in a scatter double log plot in FIG. 9. More than a 2 fold increase in mRNA expression is seen when the mRNA is outside the solid lines.

Example 3

Clinical Investigation—Treatment of Patients with Medication Resistant Major Depressive Disorder The inventors initiated a double blinded placebo controlled study on the effect of PEMF on Major Depressive Disorder. The inventors estimated a sample size of 25 patients in each group. Only patients with medication resistant Major Depressive disorder were enrolled in the study. Patients continued the antidepressive medication they had received and the dose was unchanged from 4 weeks before baseline and during the planned 5 weeks PEMF administration over 25 consecutive work days. (Monday-Friday). Each treatment session lasted 30 min. All patients had a Hamilton depression scale (HAM-D17) score of 13 or more at baseline and they were evaluated weekly over 5 weeks of trial. In all 92% of the sham treated and 91.3% of the active PEMF treated completed the 5 weeks of treatment. Table III show the results for the evaluation performed as a Hamilton score and also as a self evaluation score (VAS).

The data were evaluated by an independent statistics office and it is evident that there is a significant improvement on a Mann Whitney between group analysis after 2 weeks of treatment. When patient were self evaluating there was an improvement after visit 5.

Thus, this technology described in the patent as an add on strategy in combination with antidepressive medication and gives an improved clinical outcome as evaluated in between group analysis both on a Hamilton scale and on an self-valuation scale.

TABLE III

PEMF/LOCF

| | | Treatment | | | | | | | |
| | | Active | | | Placebo | | | | |
| Scale | Visit | N | Mean | SD | Wilcoxon | N | Mean | SD | Wilcoxon | Mann-Whitney |
|---|---|---|---|---|---|---|---|---|---|---|
| HDSTOT | Visit 1 | 23 | 20.96 | 3.98 | | 25 | 20.88 | 3.35 | | 0.9999 |
| | Visit 2 | 23 | 17.04 | 4.98 | | 25 | 19.32 | 3.01 | | 0.1106 |
| | Diff. | 23 | −3.91 | 3.26 | 0.0001 | 25 | −1.56 | 2.40 | 0.0029 | 0.0124 |
| | Visit 3 | 23 | 15.09 | 3.10 | | 25 | 17.72 | 4.30 | | 0.0082 |
| | Diff. | 23 | −5.87 | 3.05 | 0.0001 | 25 | −3.16 | 3.21 | 0.0001 | 0.0072 |
| | Visit 4 | 23 | 13.91 | 4.43 | | 25 | 17.12 | 3.99 | | 0.0038 |
| | Diff. | 23 | −7.04 | 4.32 | 0.0001 | 25 | −3.76 | 3.28 | 0.0001 | 0.0075 |
| | Visit 5 | 23 | 12.48 | 5.59 | | 25 | 16.88 | 4.28 | | 0.0047 |
| | Diff. | 23 | −8.48 | 6.04 | 0.0001 | 25 | −4.00 | 3.50 | 0.0001 | 0.0119 |
| | Visit 6 | 23 | 11.30 | 6.49 | | 25 | 16.24 | 4.77 | | 0.0044 |
| | Diff. | 23 | −9.65 | 6.93 | 0.0001 | 25 | −4.64 | 4.24 | 0.0001 | 0.0222 |
| VAS | Visit 1 | 23 | 43.22 | 10.89 | | 25 | 43.64 | 11.20 | | 0.9506 |
| | Visit 2 | 23 | 40.96 | 11.78 | | 25 | 42.40 | 10.54 | | 0.7565 |
| | Diff. | 23 | −2.26 | 5.24 | 0.0769 | 25 | −1.24 | 5.46 | 0.1577 | 0.9670 |
| | Visit 3 | 23 | 36.91 | 11.11 | | 25 | 40.32 | 12.60 | | 0.2387 |
| | Diff. | 23 | −6.30 | 3.88 | 0.0001 | 25 | −3.32 | 5.27 | 0.0051 | 0.0267 |
| | Visit 4 | 23 | 33.30 | 13.23 | | 25 | 38.20 | 12.95 | | 0.1426 |
| | Diff. | 23 | −9.91 | 7.35 | 0.0001 | 25 | −5.44 | 6.01 | 0.0001 | 0.0394 |
| | Visit 5 | 23 | 27.43 | 14.48 | | 25 | 39.00 | 14.30 | | 0.0084 |
| | Diff. | 23 | −15.78 | 13.94 | 0.0001 | 25 | −4.64 | 7.52 | 0.0030 | 0.0049 |
| | Visit 6 | 23 | 23.17 | 15.83 | | 25 | 38.96 | 14.59 | | 0.0017 |
| | Diff. | 23 | −20.04 | 17.35 | 0.0001 | 25 | −4.68 | 10.15 | 0.0353 | 0.0042 |

Example 4

Clinical Investigation—Treatment of Antidepressant Medication-Free Patients with Medication Resistant Major Depressive Disorder The study is a prospective, randomized (1:1) controlled trial comparing PEMF therapy to sham stimulation. The study period lasts up to 9 months and involves up to 20 visits. All analyses are conducted with Stata version 11 or higher software.

The study involves 60 antidepressant medication-free patients with Major Depressive Disorder who have failed at least one trial of antidepressant medication because of medication-resistance and/or medication intolerance. Patients are drug-free during the PEMF trial.

Major inclusion criteria: DSM-IV Major Depressive Disorder (MDD) without Psychotic Features. The MDD may be Recurrent or a Single Episode. The MDD may be Chronic or non-Chronic. Patients must have failed to respond to at least one antidepressant medications. The 17-item Hamilton Depression Rating Scale (HAMD17) must be 18 or greater.

Major exclusion criteria: subjects with other major psychiatric or medical disorders, patients with Bipolar Disorder I or II, patients whose current episode of major depression is longer than 5 years, patients who have failed more than 4 adequate trials of antidepressant medication, and patients who have failed to respond to at least 8 bilateral ECT.

Phase 1: Double-Blind Portion of the Study:

Medication is withdrawn over a two-week period followed by a 2-week drug-free period. At the end of the drug free period patients must still have a HAMD17 of 18 or greater.

Patients are randomly (URN randomization) assigned to PEMF or sham treatment. They receive daily PEMF treatments for a 5-week period. At the first session, the research coordinator will place the PEMF device on the head of the subject, make sure that it is properly fitted, and observe the subject for 60 minutes to make sure that it is properly used. At the second and third sessions, the subject comes to the clinic and places the PEMF device on his or her own head in the presence of the research coordinator. If the subject has properly used the PEMF device for two consecutive sessions, the subject may subsequently use the device at home.

Trained raters blind to the randomization repeat the HAMD17, HAMD6, MES, PRVSS, CGI-S, and CGI-I before the 1st and after the $7^{th}$, $14^{th}$, $21^{st}$, $28^{th}$, $35^{th}$ PEMF sessions.

Cognitive tests are done by a trained research coordinator blind to the randomization, at baseline before the 1st PEMF session and after the 35th PEMF session. These cognitive tests include: the Rey Auditory Verbal Learning Test (RAVLT), Logical Memory (Wechsler Memory Scale), Digit Symbol Test, Digit Span (WAIS-R), the Mini-Mental State Exam, Trails A and B, and the Controlled Oral Word Association Test (COWAT). The RAVLT and the Wechsler Memory Scale-Revised: Logical Memory paragraphs are included to examine immediate and delayed verbal learning and contextual verbal memory, the WAIS-R Digit Symbol Test will investigate attention and complex psychomotor speed. Trail Making A and B will measure speed of visual motor scanning and sequencing and rapidly provide a measure of cognitive flexibility to examine executive functioning. The COWAT, a language measure that has been shown to specifically activate the left frontal anterior cortical region will evaluate verbal initiation and fluency.

Phase 2: Non-remitters in Phase 1, whether they receive PEMF or Sham PEMF, have the opportunity to received real PEMF for 5 weeks (35 sessions) or until they meet remission criteria (HAMD17≤7).

The patients continue to be assessed weekly just as in Phase 1 and neuropsychological tests are done after the $35^{th}$ session.

Phase 3: For ethical reasons, remitters (HAMD17≤7) in phase 1 (whether they received PEMF or Sham PEMF) or phase 2 continuation antidepressant medication for 6 months to prevent relapse. Raters blind to the randomization will repeat the HAMD17, HAMD6, MES, PRVSS, CGI-S, and CGI-I 2 weeks, 1 month, 2 months, 3 months, 4 months, 5 months and 6 months after the last PEMF session.

Example 5

Clinical Investigation—Treatment of Patients with Parkinson's Disease

Treatment of subjects with Parkinson's disease occurs along the lines described in example 4.

Parkinson's disease is caused primarily as a result of decreased stimulation of the motor cortex by the basal ganglia, normally caused by the insufficient formation and action of dopamine. Regeneration of dopamine synapses can be attained by the PEMF technology.

REFERENCES

Thamsborg G, Florescu A, Oturai P, Fallentin E, Tritsaris K, Dissing S. *Treatment of knee osteoarthritis with pulsed electromagnetic fields: a randomized, double-blind, placebo-controlled study*. Osteoarthritis Cartilage. 2005 July; 13(7):575-81.
Rahbek U L, Tritsaris K., and Dissing S. Interactions of Low-Frequency, Pulsed Electromagnetic Fields with Living Tissue: Biochemical Responses and Clinical Results. Oral Biosciences. 2,1 29-40, 2005.
Koziesk M E, Middlemas D, Bylund D B. Brain-derived neurotrophic factor and its receptor tropomyosin-related kinase B in the mechanism of action of antidepressant therapies. *Pharmacol Ther.* 2008 January; 117(1):30-51.
Rubin C T, Donahue H J, Rubin J E, McLeod K J. Optimization of electric field parameters for the control of bone remodeling: exploitation of an indigenous mechanism for the prevention of osteopenia. *J Bone Miner Res.* 1993 December; 8 Suppl 2:S573-81.
Evans S J, Choudary P V, Neal C R, Li J Z, Vawter M P, Tomita H, Lopez J F, Thompson R C, Meng F, Stead J D, Walsh D M, Myers R M, Bunney W E, Watson S J, Jones E G, Akil H. Dysregulation of the fibroblast growth factor system in major depression. *Proc Natl Acad Sci USA.* 2004 Oct. 26; 101(43):15506-11.

The invention claimed is:

1. A non-invasive method for the treatment, relief or prophylaxis of a condition selected from the group consisting of Depression, Major Depressive Disorder, Bipolar Disorder, Epilepsy, Parkinson's Disease and Alzheimer's Disease, or for alleviating one or more symptoms associated therewith in a subject, said method comprising:
    applying a pulsed electromagnetic field trans-cranially at least to the hippocampus of said subject concomitant with administration to said subject of an antidepressant substance or compound,
        wherein said antidepressant substance or compound is selected from the group consisting of a serotonin-norepinephrine reuptake inhibitor (SNRI) and a selective serotonin reuptake inhibitor (SSRI), and
        wherein said pulsed electromagnetic field is applied with a frequency between 3-1000 Hz and a maximum field strength falls in the interval 0.02-2 V/m at a distance of 1 cm from at least one electrically conducting coil used to generate the electromagnetic field.
2. A method according to claim 1, wherein said subject receives treatment with an apparatus for stimulating brain tissue with pulsed electromagnetic fields weaker than a limit for elicitation of the action potentials of the cells of the tissue to be stimulated, said apparatus comprising:
    the at least one electrically conducting coil placed at a bitemporal position such that the hippocampus is stimulated by at least one magnetic field upon supplying a pulse to said at least one coil; and
    a pulse generation means operationally connected to said at least one coil for supplying a series of current pulses for conduction, allowing generation of pulsed magnetic fields sufficiently strong to cause protein activation, and weaker than the limit for elicitation of the action potentials of the cells of the tissue to be stimulated.
3. The method according to claim 2, wherein said apparatus comprises:
    at least five electrically conducting coils arranged in a device to be worn on the subject's head so that axes of the coils point into the head; and
    the pulse generation means is operationally connected to said at least five coils for supplying a series of bipolar square voltage pulses to each of said at least five coils resulting in a generation of a time-varying magnetic field from each of said at least five coils; wherein
        the pulses and said at least five coils are selected so that the time-varying magnetic field induces an electrical field sufficiently strong to cause protein activation, and weaker than a limit for elicitation of the action potentials of cells of the brain tissue to be stimulated, in that the electric field strength in a plane perpendicular to each of said at least five coils, a maximum field strength falls in the interval $0.5 \times 10^{-6}$ to 0.5 V/m at a distance of 10 cm from each of said at least five coils;
        the pulse generation means is configured to apply treatment in doses with bipolar square pulses supplied at a frequency of at least 20 Hz over a period of 5-120 minutes;
        at least four of said at least five coils are arranged in the device such that the hippocampus is stimulated by the induced electrical field upon supplying pulses to said at least four coils, each of said at least four coils having at least one of a temporal and parietal placement; and
        at least one of the at least five coils is arranged in the device such that the cortex is stimulated by the induced electrical field upon supplying pulses to said at least one of the at least five coils, said at least one of the at least five coils having frontal placement.
4. The method according to claim 2, wherein the electromagnetic field applied to the hippocampus provides a maximum field strength in the interval $1 \times 10^{-6}$ to 0.1 V/m at a distance of 10 cm from each of said at least five coils.
5. The method according to claim 1, wherein said pulsed electromagnetic field applied to the hippocampus is applied for a period of 5 to 120 minutes.
6. The method according to claim 1, wherein said pulsed electromagnetic field applied to the hippocampus is applied at least every third day.
7. The method according to claim 1, wherein the total number of pulses in an administered series is 5000 to 5,000,000 pulses.
8. The method according to claim 1, wherein said Serotonin-norepinephrine reuptake inhibitor is selected from the group consisting of Venlafaxine and Duloxetine.
9. The method according to claim 1, wherein said selective serotonin reuptake inhibitor is selected from the group consisting of citalopram, dapoxetine, escitalopram, fluoxetine, fluvoxamine, paroxetine,
    sertraline, and zimelidine.

10. The method according to claim 1, wherein the depression is resistant to medication with a serotonin-norepinephrine reuptake inhibitor or a selective serotonin reuptake inhibitor, without combination with activation of a pulsed electromagnetic field.

11. The method according to claim 1, further comprising assessing a level of depression in said subject before and after application of said pulsed electromagnetic field.

* * * * *